(12) United States Patent
Wieduwilt et al.

(10) Patent No.: US 12,223,550 B2
(45) Date of Patent: Feb. 11, 2025

(54) MEDICAL DIAGNOSTIC-INITIATED INSURANCE OFFERING

(71) Applicant: STATE FARM MUTUAL AUTOMOBILE INSURANCE COMPANY, Bloomington, IL (US)

(72) Inventors: Andrew Patrick Wieduwilt, Bloomington, IL (US); Leif Agerholm Roll, Bloomington, IL (US)

(73) Assignee: STATE FARM MUTUAL AUTOMOBILE INSURANCE COMPANY, Bloomington, IL (US)

( * ) Notice: Subject to any disclaimer, the term of this patent is extended or adjusted under 35 U.S.C. 154(b) by 115 days.

(21) Appl. No.: 17/963,023

(22) Filed: Oct. 10, 2022

(65) Prior Publication Data

US 2023/0032514 A1   Feb. 2, 2023

Related U.S. Application Data

(63) Continuation of application No. 17/024,839, filed on Sep. 18, 2020, now Pat. No. 11,501,382, which is a
(Continued)

(51) Int. Cl.
*G06Q 40/08* (2012.01)
*G06Q 30/08* (2012.01)
(Continued)

(52) U.S. Cl.
CPC ............ *G06Q 40/08* (2013.01); *G06Q 30/08* (2013.01); *G06Q 50/22* (2013.01); *G16H 10/60* (2018.01); *G16H 50/30* (2018.01)

(58) Field of Classification Search
CPC .... G06Q 40/08; G06Q 50/24; G06Q 30/0269; G06Q 10/0635; G16H 50/30
See application file for complete search history.

(56) References Cited

U.S. PATENT DOCUMENTS 5,794,207 A   8/1998   Walker et al.
5,797,134 A   8/1998   McMillan et al.
(Continued)

FOREIGN PATENT DOCUMENTS

AU   2008237583 A1   5/2009
CN   106663281 A     5/2017
(Continued)

OTHER PUBLICATIONS

"Assessing the Risks of Insuring Reputation Risk", Gatzert et al., Journal of Risk and Insurance, vol. 83, No. 3, 641-679 (2016) (Year 2015).
(Continued)

*Primary Examiner* — Scott S Trotter
(74) *Attorney, Agent, or Firm* — MARSHALL, GERSTEIN & BORUN LLP

(57) ABSTRACT

Techniques for initiating offers for insurance based upon medical diagnostic examinations may include, for each of a plurality of stored examination results: with a patient's or customer's affirmative consent or permission, (1) determining a health profile of a respective patient; (2) determining, based upon contents of the health profile, whether or not the patient is eligible for one or more offers of insurance; (3) providing the health profile of an eligible patient to one or more insurance providers; and/or (4) receiving one or more insurance offers that include binding quotes for insurance. Using the techniques disclosed herein, patients who have undergone medical examinations may be automatically selected and provided with insurance offers for which they have been pre-approved. The insurance offers may include binding quotes for insurance coverage. As a result, insurance or other cost savings may be provided to patients or other customers (e.g., parents of young patients).

20 Claims, 8 Drawing Sheets

Related U.S. Application Data continuation of application No. 14/871,273, filed on Sep. 30, 2015, now Pat. No. 10,817,949.

(60) Provisional application No. 62/199,008, filed on Jul. 30, 2015, provisional application No. 62/189,885, filed on Jul. 8, 2015, provisional application No. 62/173,597, filed on Jun. 10, 2015, provisional application No. 62/170,004, filed on Jun. 2, 2015, provisional application No. 62/104,596, filed on Jan. 16, 2015, provisional application No. 62/060,080, filed on Oct. 6, 2014.

(51) Int. Cl.
*G06Q 50/22* (2018.01)
*G16H 10/60* (2018.01)
*G16H 50/30* (2018.01)

(56) References Cited

U.S. PATENT DOCUMENTS

| | | |
|---|---|---|
| 5,845,255 A | 12/1998 | Mayaud |
| 6,085,169 A | 7/2000 | Walker et al. |
| 6,101,484 A | 8/2000 | Halbert et al. |
| 6,418,415 B1 | 7/2002 | Walker et al. |
| 7,107,230 B1 | 9/2006 | Halbert et al. |
| 7,194,427 B1 | 3/2007 | Van Horn et al. |
| 7,330,826 B1 | 2/2008 | Porat et al. |
| 7,343,309 B2 | 3/2008 | Ogawa et al. |
| 7,403,911 B2 | 7/2008 | Guler et al. |
| 7,490,050 B2 | 2/2009 | Grover et al. |
| 7,558,752 B1 | 7/2009 | Ephrati et al. |
| 7,584,124 B2 | 9/2009 | Porat et al. |
| 7,610,236 B2 | 10/2009 | Sandholm et al. |
| 7,685,008 B2 | 3/2010 | McGiffin et al. |
| 7,685,046 B2 | 3/2010 | Wallman |
| 7,720,743 B1 | 5/2010 | Marks |
| 7,797,194 B1 | 9/2010 | Friss et al. |
| 7,904,378 B2 | 3/2011 | Ghani et al. |
| 7,937,278 B1 | 5/2011 | Cripe et al. |
| 7,958,013 B2 | 6/2011 | Porat et al. |
| 7,979,341 B2 | 7/2011 | Hanifi |
| 7,996,296 B2 | 8/2011 | Lange |
| 8,024,203 B2 | 9/2011 | Kendall et al. |
| 8,068,475 B2 | 11/2011 | Iochi et al. |
| 8,095,399 B2 | 1/2012 | McConnell et al. |
| 8,103,577 B2 | 1/2012 | Sakaue et al. |
| 8,117,112 B2 | 2/2012 | Hambrecht et al. |
| 8,126,794 B2 | 2/2012 | Lange et al. |
| 8,176,145 B1 | 5/2012 | Stender et al. |
| 8,190,454 B2 | 5/2012 | Chien et al. |
| 8,219,423 B2 | 7/2012 | Hersch |
| 8,251,702 B2 | 8/2012 | Marks |
| 8,275,640 B2 | 9/2012 | Jayaram et al. |
| 8,296,191 B1 | 10/2012 | Foo et al. |
| 8,301,544 B2 | 10/2012 | Chatter et al. |
| 8,306,869 B2 | 11/2012 | Ford |
| 8,315,891 B2 | 11/2012 | Kendall et al. |
| 8,332,244 B1 | 12/2012 | Karam et al. |
| 8,335,701 B1 | 12/2012 | Syed et al. |
| 8,340,983 B2 | 12/2012 | Grover et al. |
| 8,341,033 B2 | 12/2012 | Porat et al. |
| 8,433,588 B2 | 4/2013 | Willis et al. |
| 8,447,637 B2 | 5/2013 | Read et al. |
| 8,515,777 B1 | 8/2013 | Rajasenan |
| 8,521,567 B2 | 8/2013 | Varanasi et al. |
| 8,527,302 B2 | 9/2013 | Johnson, Jr. et al. |
| 8,543,430 B1 | 9/2013 | Fields et al. |
| 8,545,229 B2 | 10/2013 | Marks |
| 8,577,699 B1 | 11/2013 | Diener et al. |
| 8,577,703 B2 | 11/2013 | McClellan et al. |
| 8,595,102 B1 | 11/2013 | Burdette |
| 8,600,784 B1 | 12/2013 | Ivey et al. |
| 8,612,266 B1 | 12/2013 | Ilgenfritz |
| 8,630,916 B2 | 1/2014 | Walker et al. |
| 8,635,093 B2 | 1/2014 | Kendall et al. |
| 8,639,535 B1 | 1/2014 | Kazenas |
| 8,666,786 B1 | 3/2014 | Wirz et al. |
| 8,666,788 B1 | 3/2014 | Syed |
| 8,706,531 B1 | 4/2014 | Voigt et al. |
| 8,719,063 B1 | 5/2014 | Wade et al. |
| 8,738,463 B2 | 5/2014 | Porat et al. |
| 8,744,881 B2 | 6/2014 | Reid |
| 8,799,125 B2 | 8/2014 | Schumann, Jr. |
| 8,818,618 B2 | 8/2014 | Follmer et al. |
| 8,849,803 B2 | 9/2014 | Grabau et al. |
| 9,037,394 B2 | 5/2015 | Fernandes et al. |
| 9,053,469 B1 | 6/2015 | Bohanek et al. |
| 9,269,109 B2 | 2/2016 | Berg et al. |
| 9,293,042 B1 | 3/2016 | Wasserman |
| 9,558,598 B2 | 1/2017 | Doughty et al. |
| 9,715,711 B1 | 7/2017 | Konrardy et al. |
| 9,753,987 B1 | 9/2017 | Dolan et al. |
| 9,849,364 B2 | 12/2017 | Tran et al. |
| 9,898,759 B2 | 2/2018 | Khoury |
| 9,940,676 B1 | 4/2018 | Biemer |
| 9,953,372 B1 | 4/2018 | Dziabiak et al. |
| 9,972,053 B2 | 5/2018 | Denning et al. |
| 9,996,882 B1 | 6/2018 | Manzella et al. |
| 9,996,884 B2 | 6/2018 | Collopy et al. |
| 10,062,118 B1 | 8/2018 | Bernstein et al. |
| 10,109,014 B1 | 10/2018 | Bischoff et al. |
| 10,192,265 B2 | 1/2019 | Carragher |
| 10,346,925 B2 | 7/2019 | Perl et al. |
| 10,380,693 B2 | 8/2019 | Suiter |
| 10,430,883 B1 | 10/2019 | Bischoff et al. |
| 10,467,703 B2 | 11/2019 | Olson |
| 10,475,126 B1 | 11/2019 | Clegg et al. |
| 10,489,798 B1 | 11/2019 | Madeyski |
| 10,505,726 B1 | 12/2019 | Andon et al. |
| 10,510,120 B1 | 12/2019 | Roll |
| 10,540,723 B1 | 1/2020 | Potter et al. |
| 10,580,080 B2 | 3/2020 | Rackley, III et al. |
| 10,664,920 B1 | 5/2020 | Roll et al. |
| 10,679,296 B1 | 6/2020 | Devereaux et al. |
| 10,713,718 B2 | 7/2020 | Roll et al. |
| 10,713,728 B1 | 7/2020 | Roll et al. |
| 10,817,949 B1 | 10/2020 | Wieduwilt et al. |
| 10,832,327 B1 | 11/2020 | Potter et al. |
| 10,949,928 B1 | 3/2021 | Roll |
| 2001/0004204 A1 | 6/2001 | Mitsuaki |
| 2001/0037281 A1 | 11/2001 | French et al. |
| 2001/0042041 A1 | 11/2001 | Moshal et al. |
| 2001/0056396 A1 | 12/2001 | Goino |
| 2002/0029158 A1 | 3/2002 | Wolff et al. |
| 2002/0042769 A1 | 4/2002 | Gujral et al. |
| 2002/0046067 A1 | 4/2002 | Kraehenbuehl et al. |
| 2002/0091613 A1 | 7/2002 | Kendall et al. |
| 2002/0111835 A1 | 8/2002 | Hele et al. |
| 2002/0194033 A1 | 12/2002 | Huff |
| 2003/0023492 A1 | 1/2003 | Riordan et al. |
| 2003/0050901 A1 | 3/2003 | Jester et al. |
| 2003/0069759 A1 | 4/2003 | Smith |
| 2003/0093355 A1 | 5/2003 | Issa |
| 2003/0182222 A1 | 9/2003 | Rotman et al. |
| 2003/0191672 A1 | 10/2003 | Kendall et al. |
| 2003/0208432 A1 | 11/2003 | Wallman |
| 2003/0220878 A1 | 11/2003 | Degen et al. |
| 2003/0233260 A1 | 12/2003 | Snell et al. |
| 2003/0236682 A1 | 12/2003 | Heyer |
| 2003/0236738 A1 | 12/2003 | Lange et al. |
| 2004/0010426 A1 | 1/2004 | Berdou |
| 2004/0186755 A1 | 9/2004 | Roche |
| 2005/0055299 A1 | 3/2005 | Chambers et al. |
| 2005/0071203 A1 | 3/2005 | Maus |
| 2005/0075910 A1 | 4/2005 | Solankl et al. |
| 2005/0108062 A1 | 5/2005 | Higgins |
| 2005/0119580 A1 | 6/2005 | Eveland |
| 2005/0199580 A1 | 9/2005 | Yang et al. |
| 2005/0261939 A1 | 11/2005 | Augspurger et al. |
| 2005/0278199 A1 | 12/2005 | Ghani |
| 2006/0017897 A1 | 1/2006 | Sato |
| 2006/0041500 A1 | 2/2006 | Diana et al. |

(56) References Cited

U.S. PATENT DOCUMENTS

| | | |
|---|---|---|
| 2006/0053037 A1 | 3/2006 | Kendall et al. |
| 2006/0055037 A1 | 3/2006 | Park et al. |
| 2006/0136324 A1 | 6/2006 | Barry et al. |
| 2006/0178979 A1 | 8/2006 | Levine et al. |
| 2006/0206362 A1 | 9/2006 | Rudy et al. |
| 2006/0206438 A1 | 9/2006 | Sakaue et al. |
| 2006/0241982 A1 | 10/2006 | Seifert et al. |
| 2006/0253366 A1 | 11/2006 | Rebibo |
| 2006/0265259 A1 | 11/2006 | Diana et al. |
| 2007/0226014 A1 | 9/2007 | Alemayehu et al. |
| 2007/0226015 A1 | 9/2007 | Lutnick et al. |
| 2007/0262140 A1 | 11/2007 | Long |
| 2007/0288262 A1 | 12/2007 | Sakaue et al. |
| 2008/0052111 A1 | 2/2008 | McMenimen et al. |
| 2008/0154694 A1 | 6/2008 | Litzow et al. |
| 2009/0024419 A1 | 1/2009 | McClellan et al. |
| 2009/0037228 A1 | 2/2009 | Engel |
| 2009/0055226 A1 | 2/2009 | Tritz et al. |
| 2009/0099877 A1 | 4/2009 | Hyde et al. |
| 2009/0171831 A1 | 7/2009 | Johnson, Jr. et al. |
| 2009/0182585 A1 | 7/2009 | Harkensee et al. |
| 2009/0228308 A1 | 9/2009 | Chien et al. |
| 2009/0254971 A1 | 10/2009 | Herz et al. |
| 2010/0014573 A1 | 1/2010 | Momtaz et al. |
| 2010/0131284 A1 | 5/2010 | Duffy |
| 2010/0145735 A1 | 6/2010 | Kendall et al. |
| 2010/0169126 A1 | 7/2010 | Chatter et al. |
| 2010/0198658 A1 | 8/2010 | Marks |
| 2010/0235242 A1 | 9/2010 | Firminger et al. |
| 2010/0256999 A1 | 10/2010 | Ghani et al. |
| 2011/0016687 A1 | 1/2011 | Xia |
| 2011/0021369 A1 | 1/2011 | Mhlanga et al. |
| 2011/0022417 A1 | 1/2011 | Rao |
| 2011/0047070 A1 | 2/2011 | Farias |
| 2011/0137730 A1 | 6/2011 | McCarney et al. |
| 2011/0161100 A1 | 6/2011 | Peak et al. |
| 2011/0161168 A1 | 6/2011 | Dubnicki |
| 2011/0166875 A1 | 7/2011 | Hayter et al. |
| 2011/0184250 A1 | 7/2011 | Schmidt et al. |
| 2011/0213628 A1 | 9/2011 | Peak et al. |
| 2011/0213693 A1 | 9/2011 | Kendall et al. |
| 2012/0010906 A1 | 1/2012 | Foladare et al. |
| 2012/0016692 A1 | 1/2012 | Jenkins-Robbins |
| 2012/0066007 A1 | 3/2012 | Ferrick et al. |
| 2012/0078698 A1 | 3/2012 | Pappas et al. |
| 2012/0109692 A1 | 5/2012 | Collins et al. |
| 2012/0123806 A1 | 5/2012 | Schumann, Jr. et al. |
| 2012/0123891 A1 | 5/2012 | Patel |
| 2012/0166228 A1 | 6/2012 | Singleton et al. |
| 2012/0179481 A1 | 7/2012 | Patel et al. |
| 2012/0179482 A1 | 7/2012 | Garms et al. |
| 2012/0209743 A1 | 8/2012 | Mesaros |
| 2012/0232935 A1 | 9/2012 | Voccola |
| 2012/0239438 A1 | 9/2012 | Hemmings et al. |
| 2012/0278112 A1 | 11/2012 | Hersch |
| 2012/0323697 A1 | 12/2012 | Marks |
| 2013/0013344 A1 | 1/2013 | Ernstberger et al. |
| 2013/0035964 A1 | 2/2013 | Roscoe et al. |
| 2013/0066656 A1 | 3/2013 | Hanson et al. |
| 2013/0090950 A1 | 4/2013 | Rao |
| 2013/0096956 A1 | 4/2013 | Saidel et al. |
| 2013/0117048 A1 | 5/2013 | Bradshaw et al. |
| 2013/0117049 A1 | 5/2013 | Kendall et al. |
| 2013/0151274 A1 | 6/2013 | Bage et al. |
| 2013/0166313 A1 | 6/2013 | Kitfield et al. |
| 2013/0179188 A1 | 7/2013 | Hyde et al. |
| 2013/0246151 A1 | 9/2013 | Raghavan |
| 2013/0304499 A1 | 11/2013 | Rangadass |
| 2013/0311208 A1 | 11/2013 | Lutnick et al. |
| 2013/0325517 A1 | 12/2013 | Berg |
| 2013/0328671 A1 | 12/2013 | McKown et al. |
| 2013/0339065 A1 | 12/2013 | Denning et al. |
| 2014/0006128 A1 | 1/2014 | Grigg et al. |
| 2014/0033243 A1 | 1/2014 | Chen et al. |
| 2014/0058759 A1 | 2/2014 | Hersch |
| 2014/0067428 A1 | 3/2014 | Snyder et al. |
| 2014/0067472 A1 | 3/2014 | Mayes et al. |
| 2014/0081670 A1 | 3/2014 | Lim et al. |
| 2014/0114697 A1 | 4/2014 | Denning et al. |
| 2014/0114702 A1 | 4/2014 | Grosso et al. |
| 2014/0136237 A1 | 5/2014 | Anderson et al. |
| 2014/0136443 A1 | 5/2014 | Kinsey, II et al. |
| 2014/0142987 A1 | 5/2014 | Misch et al. |
| 2014/0149148 A1 | 5/2014 | Luciani |
| 2014/0156314 A1 | 6/2014 | Gunn |
| 2014/0161721 A1 | 6/2014 | Hatchwell et al. |
| 2014/0164188 A1 | 6/2014 | Zabawa et al. |
| 2014/0164287 A1 | 6/2014 | Hyde et al. |
| 2014/0172466 A1 | 6/2014 | Kemp et al. |
| 2014/0172469 A1 | 6/2014 | Kendall et al. |
| 2014/0188525 A1 | 7/2014 | Kendall et al. |
| 2014/0222469 A1 | 8/2014 | Stahl et al. |
| 2014/0229402 A1 | 8/2014 | Caron |
| 2014/0244275 A1 | 8/2014 | Parthasarathy |
| 2014/0257047 A1 | 9/2014 | Sillay et al. |
| 2014/0257863 A1 | 9/2014 | Maastricht et al. |
| 2014/0278577 A1 | 9/2014 | Baum et al. |
| 2014/0350971 A1 | 11/2014 | Grosso et al. |
| 2014/0358592 A1 | 12/2014 | Wedig et al. |
| 2014/0372151 A1 | 12/2014 | Karamchedu et al. |
| 2014/0372228 A1 | 12/2014 | Paz-Pujalt |
| 2015/0016173 A1 | 1/2015 | Liaw |
| 2015/0025917 A1 | 1/2015 | Stempora |
| 2015/0066542 A1 | 3/2015 | Dubens |
| 2015/0066543 A1 | 3/2015 | Dubens |
| 2015/0066727 A1 | 3/2015 | Wepsic et al. |
| 2015/0066740 A1 | 3/2015 | DiCarlo |
| 2015/0081329 A1 | 3/2015 | Saidel et al. |
| 2015/0088551 A1 | 3/2015 | Morgan et al. |
| 2015/0100437 A1 | 4/2015 | Guo et al. |
| 2015/0127357 A1 | 5/2015 | Yuan et al. |
| 2015/0134344 A1 | 5/2015 | Turrentine et al. |
| 2015/0161738 A1 | 6/2015 | Stempora |
| 2015/0170287 A1 | 6/2015 | Tirone et al. |
| 2015/0172894 A1 | 6/2015 | Gabel |
| 2015/0187016 A1 | 7/2015 | Adams et al. |
| 2015/0187019 A1 | 7/2015 | Fernandes et al. |
| 2015/0206248 A1 | 7/2015 | Kornweibel et al. |
| 2015/0269681 A1 | 9/2015 | Kalinadhabhotla |
| 2015/0278855 A1 | 10/2015 | Khoury |
| 2015/0286784 A1 | 10/2015 | Hagigi et al. |
| 2015/0294420 A1 | 10/2015 | Hu |
| 2015/0324920 A1 | 11/2015 | Wilson et al. |
| 2016/0034668 A1 | 2/2016 | Rourke et al. |
| 2016/0098788 A1 | 4/2016 | Wang |
| 2016/0203278 A1 | 7/2016 | Shoemaker |
| 2016/0217512 A1 | 7/2016 | Majumdar et al. |
| 2016/0217532 A1 | 7/2016 | Slavin |
| 2016/0260175 A1 | 9/2016 | Rogers |
| 2016/0283962 A1 | 9/2016 | Chan et al. |
| 2016/0283987 A1 | 9/2016 | Nishimura |
| 2016/0314524 A1 | 10/2016 | Trindade de Sousa Monteiro |
| 2016/0335726 A1 | 11/2016 | Bonitz et al. |
| 2016/0371783 A1 | 12/2016 | Lohrmann |
| 2016/0371787 A1 | 12/2016 | Rackley, III et al. |
| 2016/0371788 A1 | 12/2016 | Rackley, III et al. |
| 2017/0061084 A1 | 3/2017 | Pandya |
| 2017/0124660 A1 | 5/2017 | Srivastava |
| 2017/0212997 A1 | 7/2017 | Buonfiglio et al. |
| 2017/0255966 A1 | 9/2017 | Khoury |
| 2018/0225770 A1 | 8/2018 | Rixford |
| 2018/0336640 A1 | 11/2018 | Dziabiak et al. |
| 2019/0220930 A1 | 7/2019 | Clark et al. |
| 2020/0294128 A1 | 9/2020 | Cella |
| 2021/0042844 A1 | 2/2021 | Potter et al. |
| 2021/0166320 A1 | 6/2021 | Roll |

FOREIGN PATENT DOCUMENTS

| | | |
|---|---|---|
| GB | 2517964 A | 3/2015 |
| JP | 2001-202473 A | 7/2001 |
| JP | 2012-003297 A | 1/2012 |
| JP | 2014-149882 A | 8/2014 |
| JP | 2016-134148 A | 7/2016 |

(56) References Cited

FOREIGN PATENT DOCUMENTS

| | | |
|---|---|---|
| KR | 20010087072 A | 9/2001 |
| KR | 20010091149 A | 10/2001 |
| KR | 20010091174 A | 10/2001 |
| KR | 20010098293 A | 11/2001 |
| KR | 20010104433 A | 11/2001 |
| KR | 20010104473 A | 11/2001 |
| KR | 20020008996 A | 2/2002 |
| KR | 20030016544 A | 3/2003 |
| KR | 101810179 B1 | 12/2017 |
| KR | 101823015 B1 | 1/2018 |
| KR | 20190071065 A | 6/2019 |
| TW | 200903372 A | 1/2009 |
| WO | WO-02/03595 A2 | 1/2002 |
| WO | WO-2017/168883 A1 | 10/2017 |

OTHER PUBLICATIONS

"Find Reliable Auto Insurance Agencies Online by Comparing Free Quotes!", PR Newswire (Mar. 3, 2017).
"Free Diagnostics? $29 Service Call?", Greenleaf Mechanical, downloaded from the Internet at: <https://www.greenleafheatingandcooling.com/free-diagnostics-service/> (Jul. 29, 2012).
"ReviMedia, Inc.; ReviMedia Re-vamps Insurance Quote Website BestQuotes.com", Insurance Business Weekly (Aug. 31, 2014).
"Signing Bonus", Wikipedia entry, downloaded from the Internet at: <https://en.wikipedia.org/w/index.php?title=Signing_bonus@oldid=476735612> (2012).
TransUnion Enters Online Auto Insurance Marketplace with the Launch of Quote Exchange, Intenret Wire (May 16, 2016).
"Use Online Auto Insurance Quotes to Review the Best Agencies in Your Area!" PR Newswire (May 6, 2016).
Douglass, Auction Rate Securities . . . Going Once, Going Twice, New Jersey CPA, Nov.-Dec. 2010.
Fleming et al., Trading Activity and Price Transparency in the Inflation Swap Market, FRBNY Economic Policy Review, May 2013.
Jaffee et al., Catastrophe Insurance, Capital Markets, and Uninsurable Risks, Journal of Risk and Insurance (1986-1998), vol. 64, Issue 2 (1997).
McLeod, Surplus lines insurers begin to make use of Web, Business Insurance, 34.37:4-6 (Sep. 11, 2000).
U.S. Appl. No. 14/871,341, Final Office Action, dated Dec. 17, 2020.
U.S. Appl. No. 14/868,864, Final Office Action, dated Dec. 28, 2020.
U.S. Appl. No. 14/868,864, Final Office Action, dated Dec. 5, 2019.
U.S. Appl. No. 14/868,864, Final Office Action, dated Nov. 16, 2018.
U.S. Appl. No. 14/868,864, Nonfinal Office Action, dated Jun. 10, 2020.
U.S. Appl. No. 14/868,864, Nonfinal Office Action, dated Jun. 11, 2018.
U.S. Appl. No. 14/868,864, Nonfinal Office Action, dated Jun. 7, 2019.
U.S. Appl. No. 14/868,874, Final Office Action, Apr. 23, 2019.
U.S. Appl. No. 14/868,874, Final Office Action, dated Dec. 13, 2019.
U.S. Appl. No. 14/868,874, Final Office Action, dated Jul. 14, 2020.
U.S. Appl. No. 14/868,874, Nonfinal Office Action, dated Apr. 2, 2020.
U.S. Appl. No. 14/868,874, Nonfinal Office Action, dated Jan. 9, 2019.
U.S. Appl. No. 14/868,874, Nonfinal Office Action, dated Oct. 1, 2020.
U.S. Appl. No. 14/868,874, Nonfinal Office Action, dated Sep. 3, 2019.
U.S. Appl. No. 14/871,170, Final Office Action, dated Apr. 19, 2019.
U.S. Appl. No. 14/871,170, Final Office Action, dated Jan. 3, 2020.
U.S. Appl. No. 14/871,170, Final Office Action, dated Jul. 2, 2021.
U.S. Appl. No. 14/871,170, Final Office Action, dated Oct. 13, 2020.
U.S. Appl. No. 14/871,170, Nonfinal Office Action, dated Apr. 6, 2020.
U.S. Appl. No. 14/871,170, Nonfinal Office Action, dated Jan. 7, 2021.
U.S. Appl. No. 14/871,170, Nonfinal Office Action, dated Jun. 27, 2019.
U.S. Appl. No. 14/871,170, Nonfinal Office Action, dated Sep. 20, 2018.
U.S. Appl. No. 14/871,230, Final Office Action, dated Jul. 23, 2021.
U.S. Appl. No. 14/871,230, Final Office Action, dated Nov. 25, 2019.
U.S. Appl. No. 14/871,230, Final Office Action, dated Oct. 14, 2020.
U.S. Appl. No. 14/871,230, Nonfinal Office Action, dated Jan. 25, 2021.
U.S. Appl. No. 14/871,230, Nonfinal Office Action, dated Jul. 12, 2018.
U.S. Appl. No. 14/871,230, Nonfinal Office Action, dated Mar. 5, 2020.
U.S. Appl. No. 14/871,230, Nonfinal Office Action, dated May 23, 2019.
U.S. Appl. No. 14/871,273, Final Office Action, dated Nov. 15, 2019.
U.S. Appl. No. 14/871,273, Nonfinal Office Action, dated Apr. 3, 2019.
U.S. Appl. No. 14/871,273, Notice of Allowance, dated Jul. 1, 2020.
U.S. Appl. No. 14/871,273, Office Action, dated Aug. 15, 2018.
U.S. Appl. No. 14/871,273, Office Action, dated Feb. 9, 2018.
U.S. Appl. No. 14/871,306, Final Office Action, dated Apr. 16, 2020.
U.S. Appl. No. 14/871,306, Final Office Action, dated Aug. 26, 2019.
U.S. Appl. No. 14/871,306, Nonfinal Office Action, dated Apr. 1, 2019.
U.S. Appl. No. 14/871,306, Nonfinal Office Action, dated Jan. 8, 2020.
U.S. Appl. No. 14/871,306, Office Action, dated Aug. 16, 2018.
U.S. Appl. No. 14/871,306, Office Action, dated Dec. 5, 2018.
U.S. Appl. No. 14/871,341, Final Office Action, dated Dec. 26, 2018.
U.S. Appl. No. 14/871,341, Final Office Action, dated Dec. 31, 2019.
U.S. Appl. No. 14/871,341, Nonfinal office action, dated Jul. 10, 2018.
U.S. Appl. No. 14/871,341, Nonfinal Office Action, dated Jun. 11, 2020.
U.S. Appl. No. 14/871,341, Office Action, dated Jun. 25, 2019.
U.S. Appl. No. 14/871,401, Final Office Action, dated Jan. 15, 2019.
U.S. Appl. No. 14/871,401, Nonfinal Office Action, dated Jul. 26, 2018.
U.S. Appl. No. 14/871,401, Notice of Allowance, dated Aug. 12, 2019.
U.S. Appl. No. 15/457,705, Final Office Action, mailed Dec. 1, 2020.
U.S. Appl. No. 15/457,705, Final Office Action, Oct. 7, 2019.
U.S. Appl. No. 15/457,705, Nonfinal Office Action, dated Jul. 2, 2020.
U.S. Appl. No. 15/457,705, Nonfinal Office Action, dated May 17, 2019.
U.S. Appl. No. 15/457,705, Roll et al., "System and Method for Obtaining and/or Maintaining Insurance Coverage", filed Mar. 13, 2017.
U.S. Appl. No. 15/704,339, Final Office Action, dated Jul. 8, 2020.
U.S. Appl. No. 15/704,339, Nonfinal Office Action, dated Jan. 2, 2020.
U.S. Appl. No. 15/704,339, Nonfinal Office Action, dated Jun. 16, 2021.
U.S. Appl. No. 15/704,339, Roll et al., "Systems and Methods for Obtaining and/or Maintaining Usage-Based Insurance", filed Sep. 14, 2017.
U.S. Appl. No. 15/704,340, Roll et al., "Systems and Methods for Obtaining and/or Maintaining Insurance for Autonomous Vehicles", filed Sep. 14, 2017.
U.S. Appl. No. 15/704,350, Final Office Action, mailed Jul. 9, 2020.

(56) References Cited

OTHER PUBLICATIONS

U.S. Appl. No. 15/704,350, Nonfinal Office Action, dated Dec. 26, 2019.
U.S. Appl. No. 15/704,350, Nonfinal Office Action, dated Jul. 8, 2021.
U.S. Appl. No. 15/704,363, Final Office Action, dated May 29, 2020.
U.S. Appl. No. 15/704,363, Nonfinal Office Action, dated Oct. 1, 2019.
U.S. Appl. No. 15/704,363, Nonfinal Office Action, dated Sep. 30, 2020.
U.S. Appl. No. 15/704,363, Roll et al., "Systems and Methods for Determining and Providing Insurance to Affinity Groups", filed Sep. 14, 2017.
U.S. Appl. No. 15/704,632, Final Office Action, dated May 22, 2020.
U.S. Appl. No. 15/704,632, Nonfinal Office Action, dated Oct. 1, 2019.
U.S. Appl. No. 15/704,632, Nonfinal Office Action, dated Oct. 2, 2020.
U.S. Appl. No. 15/704,632, Roll et al., "Systems and Methods for Obtaining and/or Securing Insurance for Affinity Groups", filed Sep. 14, 2017.
U.S. Appl. No. 15/869,685, Nonfinal Office Action, dated Aug. 21, 2019.
U.S. Appl. No. 15/869,685, Notice of Allowance, mailed Mar. 5, 2020.
U.S. Appl. No. 15/869,685, Roll et al., "Risk Mitigation for Affinity Groupings", filed Jan. 12, 2018.
U.S. Appl. No. 15/869,752, Nonfinal Office Action, dated Oct. 31, 2019.
U.S. Appl. No. 15/869,752, Notice of Allowance, Apr. 14, 2020.
U.S. Appl. No. 15/869,752, Roll et al., "Blockchain System and Methods for Providing Insurance to Affinity Groups", filed Jan. 12, 2018.
U.S. Appl. No. 16/679,768, Nonfinal Office Action, dated Oct. 1, 2020.
U.S. Appl. No. 16/679,768, Roll et al., System and Method for Obtaining and/or Maintaining Insurance Coverage, filed Nov. 11, 2019.
U.S. Appl. No. 16/853,691, Nonfinal Office Action, dated Sep. 21, 2021.
U.S. Appl. No. 16/853,691, Roll et al., "Blockchain Systems and Methods for Providing Insurance Coverage to Affinity Groups", filed Apr. 20, 2020.
U.S. Appl. No. 16/853,693, Nonfinal Office Action, dated Sep. 14, 2021.
U.S. Appl. No. 16/853,693, Roll et al., "Blockchain Systems and Methods for Providing Insurance Coverage to Affinity Groups", filed Apr. 20, 2020.
U.S. Appl. No. 16/853,699, Nonfinal Office Action, dated Sep. 29, 2021.
U.S. Appl. No. 16/853,699, Roll et al., "Blockchain Systems and Methods for Providing Insurance Coverage to Affinity Groups", filed Apr. 20, 2020.
U.S. Appl. No. 16/853,704, Nonfinal Office Action, dated Sep. 14, 2021.
U.S. Appl. No. 16/853,704, Roll et al., "Blockchain Systems and Methods for Providing Insurance Coverage to Affinity Groups", filed Apr. 20, 2020.
U.S. Appl. No. 16/853,706, Nonfinal Office Action, dated Oct. 6, 2021.
U.S. Appl. No. 16/853,706, Roll et al., "Blockchain Systems and Methods for Providing Insurance Coverage to Affinity Groups", filed Apr. 20, 2020.
U.S. Appl. No. 16/853,711, Nonfinal Office Action, dated Sep. 29, 2021.
U.S. Appl. No. 16/853,711, Notice of Allowance, dated Mar. 18, 2022.
U.S. Appl. No. 16/853,711, Roll et al., "Blockchain Systems and Methods for Providing Insurance Coverage to Affinity Groups", filed Apr. 20, 2020.
U.S. Appl. No. 16/892,500, Nonfinal Office Action, dated Feb. 1, 2022.
U.S. Appl. No. 16/892,500, Roll et al., "Risk Mitigation for Affinity Groupings", filed Jun. 4, 2020.
U.S. Appl. No. 16/910,687, Nonfinal Office Action, dated Mar. 16, 2022.
U.S. Appl. No. 16/910,687, Roll et al., "Machine Learning Technologies for Efficiently Obtaining Insurance Coverage", filed Jun. 24, 2020.
U.S. Appl. No. 16/910,695, Nonfinal Office Action, Feb. 17, 2022.
U.S. Appl. No. 16/910,695, Roll et al., "Affinity Group Auctions for Reinsurers", filed Jun. 24, 2020.
U.S. Appl. No. 16/910,702, Nonfinal Office Action, dated Mar. 28, 2022.
U.S. Appl. No. 16/910,702, Roll et al., "Systems and Methods for Efficiently Reinsuring Insurance Policies", filed Jun. 24, 2020.
U.S. Appl. No. 16/934,565, Final Office Action, dated Jul. 13, 2022.
U.S. Appl. No. 16/934,565, Nonfinal Office Action, dated Mar. 17, 2022.
U.S. Appl. No. 17/024,839, Nonfinal Office Action, dated Jul. 11, 2022.
U.S. Appl. No. 17/024,839, Notice of Allowance, dated Sep. 8, 2022.

MEDICAL DIAGNOSTIC-INITIATED INSURANCE OFFERING

CROSS-REFERENCE TO RELATED APPLICATIONS

This application is a continuation of U.S. patent application Ser. No. 17/024,839, which was filed on Sep. 18, 2020, which is a continuation of U.S. patent application Ser. No. 14/871,273, which was filed on Sep. 30, 2015, and which claims priority to and the benefit of:
U.S. Provisional Application No. 62/060,080 filed on Oct. 6, 2014 and entitled "System and Method for Obtaining and/or a Maintaining Insurance Coverage,"
U.S. Provisional Application No. 62/104,596 filed on Jan. 16, 2015 and entitled "System and Method for Obtaining and/or a Maintaining Insurance Coverage,"
U.S. Provisional Application No. 62/170,004 filed on Jun. 2, 2015 and entitled "Systems and Methods for Initiating the Procurement of Insurance Based Upon Medical Diagnostic Examinations,"
U.S. Provisional Application No. 62/173,597 filed on Jun. 10, 2015 and entitled "Medical Diagnostic-Initiated Insurance Offering,"
U.S. Provisional Application No. 62/189,885 filed on Jul. 8, 2015 and entitled "System and Method for Obtaining and/or a Maintaining Insurance Coverage," and
U.S. Provisional Application No. 62/199,008 filed on Jul. 30, 2015 and entitled "System and Method for Obtaining and/or a Maintaining Insurance Coverage," the entire disclosures of which are hereby incorporated herein by reference.

FIELD OF THE DISCLOSURE

The present disclosure generally relates to insurance and, more specifically, to systems and methods for initiating the procurement of insurance coverage based upon medical diagnostic examinations.

BACKGROUND

Individuals who seek to be covered by health-related insurance and are sensitive to pricing and product features (e.g., coverage types and/or limits, deductibles, etc.) often expend considerable time and effort in finding insurance providers that best meet their needs. Some types of insurance require a medical diagnostic examination to be performed on the potential insured party or insuree prior to generating and offering a binding quote, for example, life insurance, long-term care insurance, disability insurance, health insurance, etc. Conventionally, a consumer seeking such insurance (e.g., via in an agent, online, mobile device, a tablet, a computing device, a call center, etc.) submits partial personal information to receive ballpark quotes for premium payments for a face value of an insurance policy. The partial personal information typically may include answers to a set of questions about the potential insured party that are provided by the potential insured party and/or by his or her agent. Examples of such partial personal information include gender; age; state and/or ZIP Code; height and weight; whether or not the potential insured party uses tobacco products or not; whether or not the potential insured party has certain medical conditions such as high blood pressure, elevated cholesterol, depression, diabetes, etc.; whether or not any of the parents and/or siblings of the potential insured party have been diagnosed with medical conditions such as cancer, stroke and/or heart condition, etc.; and a general self-categorization of his or her health, e.g., fair, good, very good, excellent, etc.

In some scenarios, one or more desired insurance terms such as coverage amount, monthly premium amount, etc. may be submitted. Accordingly, the initiation of the procurement of insurance may be triggered by the submission, by a potential insured party or by an agent of the potential insured party, of partial personal information of the potential insured party to one or more insurance providers.

After the partial personal information has been submitted to and processed by one or more recipient insurance providers, the consumer may receive one or more estimates, ballpark quotes, and/or non-binding quotes for one or more possible insurance policies. Subsequently, the consumer may select a particular non-binding quote offered by a particular insurance carrier or provider (typically, based upon the premium payment amount), and may be required by the particular insurance carrier provider to undergo a medical diagnostic examination as part of the application process.

The results of the medical diagnostic examination may then be utilized to determine whether or not the potential insured party actually meets the insurance carrier or provider's risk profile for the particular insurance policy. If the results of the medical diagnostic examination (and, in some cases, other additional information) indicate that the potential insured party meets the risk profile or otherwise is an eligible insured party for the particular insurance policy, the insurance carrier or provider may generate a binding quote for the particular insurance policy based upon the results, and offer it to the consumer.

This conventional approach suffers from several drawbacks. For instance, a consumer may be required to submit partial personal information without knowing if he or she is actually medically eligible for the insurance policy being quoted. If he or she is not medically eligible as eventually is determined based upon his or her medical diagnostic examination results, the consumer may be required to adjust his or her desired insurance terms and resubmit his or her personal information in hopes of finding a suitable insurance policy for which he or she is eligible. This cycle may need to be repeated multiple times and as such, the consumer may be required to go through multiple redundant steps in order to eventually find a suitable policy.

Further, the initially provided non-binding quote may differ from the actual binding quote to a significant extent. In such situations, the consumer may again repeat the cycle in hopes of finding a suitable insurance premium amount. Thus, the consumer may be forced to guess at what particular terms will result in a suitable insurance policy for which he or she is an eligible insured party based upon the results of his or her yet-to-be-performed medical diagnostic examination.

SUMMARY

The present embodiments may, inter alia, automatically provide a consumer or patient with one or more offers for insurance corresponding to one or more health-related insurance policies for which the patient is an eligible insured party based upon the patient's medical diagnostic examination results, without requiring the patient to submit partial personal information and/or without requiring the patient to cyclically hone in on acceptable insurance terms. In some embodiments, insurance for the patient may automatically be procured and bound upon the initial availability of medical diagnostic examination results. Examples of such types of insurance may include life insurance (e.g., term, whole life, universal life, etc.), disability insurance, long-term care insurance, and health insurance, to name a few. The initial provision of insurance offers may include one or more binding quotes, and the generation of the one or more binding quotes may be automatically triggered when the results of a medical diagnostic examination that has been performed on a patient are newly or initially determined and/or available.

Indeed, the generation of the one or more binding quotes may be automatically triggered based upon the initial availability of the examination results, and the one or more binding quotes may be the first or initial estimates or quotes for insurance based upon the newly available results which the consumer receives. In some embodiments, insurance may be automatically procured for the patient when the newly available examination results are initially made available. Thus, the time and/or effort that consumers must spend to find a suitable insurance policy may be greatly reduced or even eliminated.

In an aspect, a system for triggering the initiation of offers for insurance based upon medical diagnostic examination results may be provided. The system may be operated by a medical diagnostic provider and/or by an insurance procurer, for example. The system may include one or more data storage devices storing thereon results of a plurality of medical diagnostic examinations that have been performed by one or more medical diagnostic providers on a respective plurality of patients or subjects. Additionally, the system may include a network interface that communicatively couples the system to the system(s) of one or more insurance providers. The system may further include one or more processors and one or more memories that are particularly configured with particular computer-executable instructions.

The particular computer-executable instructions, when executed by the one or processors of the system, may cause the system to determine, for each set of medical examination results that are stored in the data storage devices, whether or not the contents of a health profile of the respective patient or subject renders the respective patient or subject as eligible for one or more offers for one or more types of insurance that require an applicant or potential insured party to undergo a medical diagnostic examination, e.g., life insurance, long-term care insurance, disability insurance, health insurance, and/or another type of health-related insurance. The health profile may be determined, for example, based upon information and/or data included in the results of the respective patient's medical diagnostic examination, which may have included at least one invasive procedure such a blood draw, and/or which may have been performed during the patient's annual physical examination. When a patient or subject is determined to be eligible, the particular computer-executable instructions may be executed to provide, via the network interface, the health profile of the patient or subject to one or more insurance provider computing systems for the generation of one or more binding quotes for insurance. Indeed, the patient or subject's health profile may be the initial and/or the sole or only indication of the patient or subject's quality of health that is received by the recipient insurance provider computing systems and that is used by the recipient insurance provider computing systems to determine the terms of the one or more binding quotes. At least some of the recipient insurance provider computing systems may return one or more binding quotes for one or more insurance policies for which the patient or subject is eligible as an insured party. As such, the instructions may be executed to further receive, via the network interface, the one or more binding quotes for one or more respective insurance policies for which the respective patient is eligible to be an insured party. The particular computer-executable instructions may be further executed to provide indications of the one or more binding quotes to a user, thereby initiating the one or more offers for one or more types of insurance.

In one embodiment, the computer-executable instructions may be further executable to cause the system to, when the respective patient is determined to be eligible to receive insurance offers, receive an indication of a selection of one of the binding quotes, and provide an indication of the selected binding quote to the insurance provider system from which the quote was received. In some cases, the computer-executable instructions may be further executable to cause the system to receive an indication that the selected binding quote has been bound by the insurance provider, and cause at least a portion of the cost to perform the medical diagnostic examination to be credited or refunded to the respective patient.

In one embodiment, the one or more binding quotes that are received by the system may correspond to multiple types of insurance policies. Additionally or alternatively, the one or more binding quotes may have been determined based upon one or more preferred insurance policy parameters or terms such as a premium payment amount, a term length, a rating of a potential insurance provider, a desired type of insurance, a payout amount, an annuity amount, a settlement option, and/or others. One or more of the preferred insurance policy parameters or terms may have been indicated by the patient, the patient's agent, or the insurance provider, for example.

The system may include additional, fewer, or alternate elements, including those discussed elsewhere herein. Further, some or all elements of the system may perform one or more portions of any of the methods described herein.

In an aspect, a computer-implemented method for initiating offers for insurance based upon medical diagnostic examinations via an electronic or communications network is provided. The method may include, for each medical diagnostic examination included in a plurality of medical diagnostic examinations that have been performed by a medical diagnostic provider on a plurality of subjects and whose respective results are stored in one or more data storage devices, determining, by using one or more processors of a first computing system and based upon a health profile of a respective subject of the each medical diagnostic examination, whether or not the respective subject is eligible for one or more offers for one or more types of insurance that require a medical diagnostic examination to be performed on a potential insured party, e.g., life insurance, disability insurance, long-term care insurance, health insurance, and/or another type of health-related insurance. The health profile of the respective subject may have determined based upon the results of the each medical diagnostic examination, which may have included at least one invasive procedure such as a blood draw, and/or may have been performed as part of the respective subject's annual physical examination.

When the respective subject of the each medical diagnostic examination is determined to be eligible for the one or more offers for the one or more types of insurance, the method may include providing, using a network interface of the first computing system and via the electronic or communications network, the health profile of the respective subject to a computing system that is operated and/or provided by an insurance provider; and receiving, via the network interface of the first computing system and the electronic or communications network from the insurance provider computing system, one or more binding quotes for one or more respective insurance policies for which the respective subject is eligible to be an insured party. Each of the one or more binding quotes may have been determined based upon the health profile of the respective subject, and the health profile may have been a sole indication of a quality of health of the respective subject that is received by the insurance provider computing system that corresponds to a generation of the one or more binding quotes. Further, the method may include causing, by the one or more processors of the first computing system, respective indications of the one or more binding quotes for the one or more respective insurance policies to be presented at a user interface, thereby initiating the one or more offers for the one or more types of insurance.

In one embodiment, when the respective subject of the each medical diagnostic examination is determined to be eligible to receive the one or more offers for the one or more types of insurance, the method may further include receiving an indication of a selection of one of the one or more binding quotes, and providing, to the insurance provider computing system, an indication that the one of the one or more binding quotes has been selected. In some cases, the method may include receiving an indication that the selected binding quote has been bound by the insurance provider, and refunding and/or crediting a cost of the each medical diagnostic examination performed on the respective subject upon receiving the indication that the selected binding quote has been bound.

In one embodiment, the first computing system may be operated and/or provided by the medical diagnostic provider, and the one or more data storage devices may be included in the first computing system.

In one embodiment, the method may include generating, by the one or more processors of the first computing system, the health profile of the respective subject based upon the stored results of the each medical diagnostic examination. Additionally or alternatively, the method may include providing, to the insurance provider computing system, one or more preferred insurance policy terms in conjunction with the health profile of the respective subject. The insurance provider computing system may generate at least one of the one or more binding quotes based on the one or more preferred insurance policy parameters or terms. The one or more preferred insurance policy parameters or terms may include an amount of a premium payment, a term length, an insurance provider rating, a desired type of insurance, a payout amount, an annuity amount, a settlement option, and/or another insurance policy term. At least one of the one or more preferred insurance policy terms may be defined or indicated by the respective subject, an agent of the respective subject, and/or the insurance provider, for example.

In one embodiment, the method may include selecting, by using the one or more processors of the first computing system, the insurance provider from a plurality of insurance providers based upon the health profile of the respective subject and/or the one or more types of insurance.

The method may include additional, fewer, or alternate actions, including those discussed elsewhere herein. Further, some or all of the method may be performed by any of the systems described herein, and/or in conjunction with one or more portions of any number of the other methods described herein.

With the present embodiments, a customer may first opt into a program or agreement (e.g., one offered by an intermediary entity such as the entity associated with computing system 14 of FIG. 1), and willingly share his or her personal data (and/or vehicle data, health data, mobile device data, etc.) for purposes of obtaining insurance coverage. In return, the customer may obtain one or more benefits that may be provided by various embodiments described herein, such as superior insurance rates/terms, and/or automatic renewal (or change) of insurance policies with little or no effort by the customer, for example. In some embodiments, customers who opt in may also receive other benefits, such as insurance discounts or rewards, for example.

Advantages will become more apparent to those skilled in the art from the following description of the preferred embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

BRIEF DESCRIPTION OF THE DRAWINGS

The Figures described below depict various aspects of the system and methods disclosed therein. It should be understood that each Figure depicts an embodiment of a particular aspect of the disclosed system and methods, and that each of the Figures is intended to accord with a possible embodiment thereof. Further, wherever possible, the following description refers to the reference numerals included in the following Figures, in which features depicted in multiple Figures are designated with consistent reference numerals.

There are shown in the drawings arrangements which are presently discussed, it being understood, however, that the present embodiments are not limited to the precise arrangements and instrumentalities shown, wherein.

Figure 1:
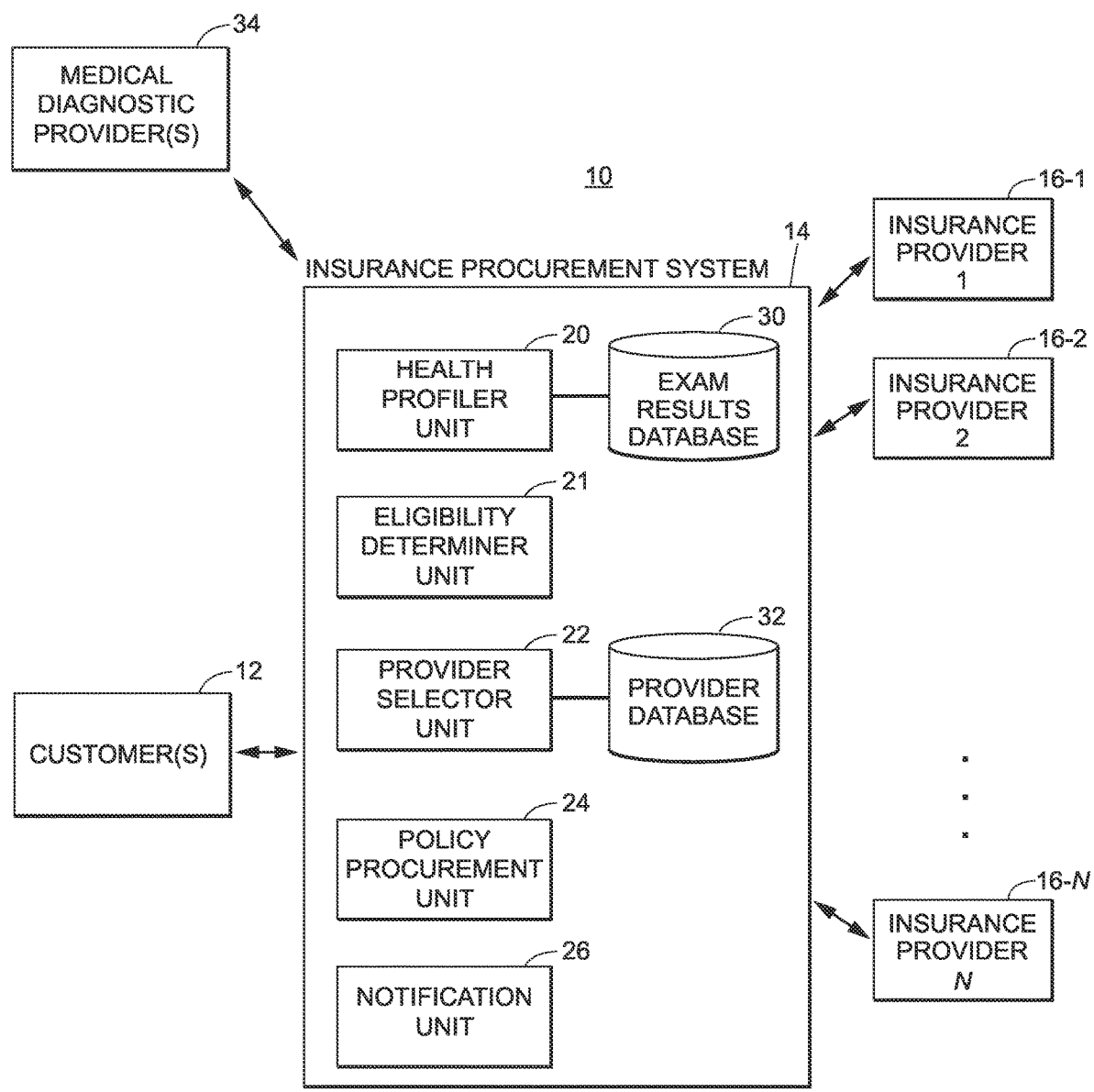
FIG. 1 depicts an exemplary environment including components associated with providing insurance and/or insurance offers based upon medical diagnostic examinations, according to one embodiment.

The Figures depict preferred embodiments for purposes of illustration only. One skilled in the art will readily recognize from the following discussion that alternative embodiments of the systems and methods illustrated herein may be employed without departing from the principles of the invention described herein.

DETAILED DESCRIPTION

I. Exemplary Environment for Medical Diagnostic Examination-Initiated Insurance Offers and/or Procurement The present embodiments relate to, inter alia, automatically initiating procurement of insurance for types of insurance that require a medical diagnostic examination to be performed on a potential insured party. Examples of such types of insurance may include life insurance (e.g., term, whole life, universal life, etc.), disability insurance, long-term care insurance, and health insurance, to name a few.

Generally, the techniques disclosed herein may allow patients or potential consumers to automatically receive one or more binding quotes for one or more insurance policies for which they are eligible or have been pre-approved as an insured party after the patient has undergone a medical diagnostic exam, without requiring the consumer to initially submit any partial personal information, and/or without requiring the patient or consumer to guess at or predict which specific insurance terms may eventually render the patient as eligible or approved for health-related insurance coverage. In some cases, the techniques disclosed herein the automatic procurement of insurance includes automatically establishing an in-force insurance policy based upon the patient's medical diagnostic examination results.

In one embodiment, the techniques disclosed herein may include selecting a set of patients who have been determined to be eligible insured parties of particular insurance offer(s) based upon their medical diagnostic examination results, and triggering the initial provision of the insurance offers. The completion of a particular patient's medical diagnostic examination and the initial availability of its results may automatically trigger the procurement of insurance for which the particular patient is an eligible, pre-approved party.

Generally, the offered and/or procured health-related insurance is/are types of insurance that require a medical diagnostic examination to be performed on a potential insured party, and as such, the techniques disclosed herein initially provide the patients with insurance and/or insurance offers for which they have been pre-approved. For ease of discussion herein, a "customer," "consumer," or "patient" generally refers to a person who has undergone a medical diagnostic examination, and who is a potential insured party or insuree of (i.e., potentially will be covered by) one or more health-related insurance policies. However, any number of the techniques described herein may equally apply to situations in which a "consumer" is an agent of the patient or potential insured party, e.g., a parent of a minor for which insurance coverage is desired, a person who has power of attorney for a potential insured party, etc.

With regard to medical diagnostic-initiated insurance offerings, a patient or potential insured party may undergo a medical diagnostic examination. Typically, the medical diagnostic examination is physically performed on the patient by a medical diagnostic provider, such as a physician or other medical professional, a medical diagnostics laboratory, or the like. The medical diagnostic examination may include one or more invasive procedures, such as a blood draw and respective analysis, a rectal exam, etc. Additionally or alternatively, the medical diagnostic examination may include one or more other non-invasive procedures, such as taking measurements (e.g., weight, blood pressure, etc.), palpation, or obtaining a culture. The medical diagnostic examination may be an annual physical examination, for example.

In some embodiments, prior to or as part of the medical diagnostic examination, the patient (and/or his or her agent) may give permission, affirmative consent or assent to initiating the automatic procurement of insurance when the exam results are made available, for example, by authorizing or granting permission for the release of his or her medical information and/or by waving his or her right to privacy. Additionally or alternatively, the patient (and/or his or her agent) may give permission for health-related insurance to be obtained (and in some cases, enacted as an in-force insurance policy) on his or her behalf.

The result of the medical diagnostic examination may be stored, e.g., in a medical records database and/or other database. The results of the patient's medical diagnostic examination may be stored at an insurance procurement system which, in one embodiment, may be owned and/or operated by the medical diagnostic provider. In some embodiments, the results of the patient's medical diagnostic examination may be stored at the medical diagnostic provider system or at a third party system under the direction of the medical diagnostic provider system, but nonetheless be made available to the insurance procurement system. The insurance procurement system may automatically operate on stored medical examination results (with customer permission) to determine if a particular patient for whom results have been newly added is eligible for one or more types of insurance policies for which medical diagnostic examinations are a pre-requisite. Additionally or alternatively, the insurance procurement system may operate on a plurality of stored medical examination results to determine which of the corresponding patients are eligible for one or more types of insurance policies for which medical diagnostic examinations are a pre-requisite. In some situations, the insurance procurement system may automatically act on a particular patient or consumer's behalf (with customer permission) to automatically determine, based upon the results of the patient's medical diagnostic examination, one more insurance carriers or providers that are able to offer insurance policies that best meet the consumer's need, e.g., by using an online or other auction model.

In one example, the insurance procurement system may automatically generate a health profile of the patient based upon his or her stored medical diagnostic examination results and provide the health profile of the patient or consumer (and, optionally, an indication of one or more patient or consumer preferences and/or requirements) to computing systems of one or more insurance carriers or providers for bidding. The insurance providers' computing systems may return bids and/or offers for insurance that have been tailored to the patient or consumer, and/or for which the patient or consumer has been determined to be an eligible or approved insured party. Such offers may include binding quotes, as the offers were generated based upon the results of a comprehensive medical diagnostic examination of the patient.

The binding quotes may be the initial, first, or only estimates of quotes for insurance (either binding or non-binding) that are generated by the insurance providers' computing systems corresponding to the consumer or patient. Similarly, the binding quotes may be the initial, first, or only estimates of quotes for insurance (either binding or non-binding) that the consumer or patient is provided based upon his or her available (and in some cases, newly available) medical diagnostic examination results. Subsequently, in some embodiments, the insurance procurement system may select one of the offers for insurance on behalf of the patient or consumer, e.g., based upon consumer preferences and/or requirements, thereby entering into a contract for insurance on behalf of the patient or consumer.

In another example, the insurance procurement system may automatically generate a health profile of a patient (with customer permission) based upon his or her medical diagnostic examination results, and/or may provide the health profile the patient (and, optionally, an indication of one or more consumer preferences and/or requirements) to computing systems of one or more insurance carriers or providers. The insurance providers computing systems may return offers for insurance that have been determined based upon the patient's health profile and, optionally, on the one or more consumer preferences and/or requirements. Typically, the offers for insurance may include binding quotes. The insurance procurement system may cause indications of the offers for insurance to be presented to a user, and/or may receive a user selection of one of the offers. The insurance procurement system may then provide, to the insurance provider computing system from which the selected offer was received, an indication that the selected offer was chosen by the user.

In yet another example, each set of stored medical examination results for a set of patients may be used to determine a respective health profile of each patient included in the set. Based upon the contents of a given health profile, the insurance procurement system may determine whether or not the corresponding patient is eligible as an insured party for one or more offers of one or more types of insurance. If the patient is eligible, the insurance procurement system may provide the health profile of the patient (and, optionally, an indication of one or more preferences and/or requirements on an insurance policy and/or insurance provider) to one or more computing systems of one or more insurance carriers or providers. The insurance providers' computing systems may return offers for insurance that have been tailored to the patient and for which the patient has been already determined to be an eligible or approved insured party. Such offers may include binding quotes, as the offers were generated based upon the results of the comprehensive medical diagnostic examination of the patient, as indicated in the health profile. The binding quotes may be the initial, first, sole, or only estimates or quotes (either binding or non-binding) for insurance that the patient and/or his or her agent is provided or notified of based upon his or her medical diagnostic examination results.

By using one or more of the techniques described above, consumers may be able to automatically obtain offers for insurance and/or enacted, in-force insurance coverage at the most competitive price and/or with the most desired features without the hassles of shopping for insurance on their own. In fact, the completion of the medical diagnostic examination may initiate or trigger the automatic procurement and/or enactment of insurance coverage on behalf of a consumer or patient from the most recent or immediate results of his or her medical diagnostic examination, thus saving the consumer or patient from needing to initiate the procurement process and provide partial personal information, as well as from lengthy delays and repetitive actions. For example, an online or other auction for possible insurance policies for the consumer or patient may be triggered and procured by a completion of the patient's annual physical. As such, the insurance procurement process may be streamlined and take less time to complete, and may provide more accurate, initial binding quotes to the consumer or patient.

II. Exemplary Environment for Automatically Initiating Insurance Coverage Based Upon Medical Diagnostic Exams FIG. 1 depicts an exemplary environment 10 including components associated with obtaining insurance offers and/or insurance coverage that is triggered or initiated based upon completion of or completed medical diagnostic examinations, according to one embodiment. As illustrated in FIG. 1, the environment 10 may include a computing device 12 that is operated by a consumer, patient, or customer, or by an agent thereof. The computing device 12 may be any suitable type of computing device having wired and/or wireless communication capabilities, such as a personal computer, tablet, phablet, smartphone, etc.

The environment 10 may include an insurance procurement system 14, which may comprise a computing system. The insurance procurement system 14 may include one or more servers, or may include a plurality of networked computing devices that have an appearance of a single, logical computing device or system, e.g., a group of cloud computing devices, a peer group of computing devices, or the like. The insurance procurement system 14 may be communicatively coupled to the computing device 12 via one or more electronic or communications networks (not shown in FIG. 1). The one or more electronic or communications networks may be a single network, or may include multiple networks of one or more types (e.g., one or more wired and/or wireless local area networks (LANs), and/or one or more wired and/or wireless wide area networks (WANs) such as the Internet), for example.

The environment 10 may include computing systems 16-1 through 16-N associated with N respective insurance carriers or providers (e.g., two insurance providers, five insurance providers, etc.). Each of the computing systems 16-1 through 16-N may include one or more servers of the respective insurance provider, or may include a plurality of networked computing devices that have an appearance of a single, logical computing device or system, e.g., a group of cloud computing devices, a peer group of computing devices, or the like. Each of the insurance provider computing systems 16-1 through 16-N may be communicatively coupled to insurance procurement system 14 via one or more electronic or communications networks (not shown in FIG. 1). The one or more electronic or communications networks may be a single network, or may include multiple networks of one or more types (e.g., one or more wired and/or wireless LANs, and/or one or more wired and/or wireless WANs such as the Internet), for example. Each of the insurance providers 16-1 through 16-N may be a company or organization providing a particular type or types of insurance that require a potential insured party to undergo a medical diagnostic examination, the results of which are used to determine insurance policy terms, e.g., health-related insurance. Examples of such types of insurance may include life insurance (e.g., term, whole life, universal life, etc.), disability insurance, long-term care insurance, and health insurance, to name a few.

The insurance procurement system 14 may include various units, including a health profiler unit 20, an eligibility determiner unit 21, a provider selector unit 22, a policy procurement unit 24 and/or a notification unit 26. Each of some or all of the units 20, 21, 22, 24 and 26 may be (or may include) a respective set of one or more computing devices or processors that executes software or computer-executable instructions to perform the corresponding functions described herein. Alternatively, each of some or all of the units 20, 21, 22, 24 and 26 may be, or include, a respective component of software or set of computer-executable instructions that is stored on one or more tangible, non-transitory computer-readable media (e.g., a random access memory (RAM) and/or read-only memory (ROM) of the insurance procurement system 14) and that is executed by one or more processors of the insurance procurement system 14 to perform the corresponding functions described herein. Still additionally or alternatively, each of some or all of the units 20, 21, 22, 24 and 26 may at least partially comprise hardware and/or firmware. Further, one or more of the units 20, 21, 22, 24 and 26 may be combined into a single unit, or may be omitted. In various different embodiments, for example, the insurance procurement system 14 may not include the eligibility determiner unit 21, the provider selector unit 22, and/or the notification unit 26.

In one embodiment, the health profiler unit 20 may determine a health profile of a patient (with patient permission) based upon the results of a medical diagnostic examination that has been performed on the patient. The patient's medical diagnostic examination results (or portions thereof) may be received at the insurance procurement system 14 from a system 34 provided by the medical diagnostic provider of the patient, and the received results may be stored in an examination results database or data storage entity 30, which may be configured to store the medical diagnostic examination results of multiple patients. The examination results database 30 may be any suitable type of persistent memory, and may comprise one or more data storage devices that have the appearance of a single, logical data storage device. The health profiler unit 20 may obtain at least some of the data included in the patient's stored, medical diagnostic examination results. Additionally or alternatively, the health profiler unit 20 may be triggered to determine the health profile of a patient when corresponding examination results are stored into the data base 30. For example, the act of initially storing a new set of examination results may trigger the health profiler unit 20 to generate a corresponding health profile. Additionally or alternatively, the health profiler unit 20 may regularly scan the database 30 for newly added examination results and/or generate new health profiles therefrom (with patient permission), and/or the health profiler unit 20 may determine health profiles when directed to by a user or by another system.

The health profiler unit 20 may utilize the obtained examination results data to generate a health profile of the patient (with patient permission). Generally speaking, the medical diagnostic examination results of the patient may include measurements, analysis results, observations or comments provided by a medical professional, and/or any other data or information that was obtained during and/or as a result of the performance of the medical diagnostic examination. On the other hand, a health profile of the patient generally includes a subset of the information stored in the patient's examination results, e.g., the subset of information which may be utilized by an insurance provider to determine whether or not the patient meets the insurance providers risk profile for various insurance policies.

For example, a patient's health profile may include types of diagnostic examination results or data that have been pre-determined to be statistically significant in determining and/or defining the terms of an insurance policy, and an insurance provider may utilize the health profile to determine whether or not a patient is an acceptable risk for various insurance policies. The health profile may include characterizations and or categorizations of various aspects of the patient's health that were determined based upon one or more data points of the stored, medical diagnostic exam results. In some cases, the subset of information may include aggregated, averaged, or otherwise combined data from the stored, medical diagnostic exam results of the patient. The content and format of the patient's health profile may be consistent with that utilized by insurance providers for ease and convenience of use.

An eligibility determiner unit 21 of the insurance procurement system 14 may determine (with patient permission), based upon the contents of a health profile, whether or not the corresponding patient is potentially eligible for one or more offers for one or more types of insurance that require a medical diagnostic examination to be performed on a potential insured party. The determination may be based upon, for example, data and/or information included in the health profile of the patient. Additionally or alternatively, the determination may be made based upon, for example information, data, boundary conditions, and/or other criteria provided by each of the insurance providers 16-1 to 16-N, the medical diagnostic provider 34, the insurance procurer 14, and/or in some cases, by the patient or the patient's agent.

The information, data, boundary conditions, and/or other criteria that are provided by each of the insurance providers 16-1 to 16-N and/or by the medical diagnostic provider 34 may be stored in a provider database 32, in one embodiment, and may be accessed by the eligibility determiner unit 21 and/or by the provider selector unit 24. The provider database 32 may be any suitable type of persistent memory, and may comprise one or more data storage devices that have the appearance of a single, logical data storage device, although in some cases, the examination results database 30 and the provider database 32 may an integral database.

The information, data, boundary conditions, and/or other criteria that are provided by the patient or the patient's agent may include preferences for and/or requirements on the insurance policies, offers, and/or the insurance carriers or providers, and may be stored in conjunction with the patient's examination results, e.g. in conjunction with the patient's medical diagnostic examination results in the examination results database 30, and/or in another database. For example, one or more desired and/or required insurance policy terms may be indicated a priori and used to perform the selection. Such desired and/or required terms may include, for example, a premium amount, a length of term, an insurance provider rating, a desired type of insurance, a payout or face value amount, a cash surrender value, a dividend, a lapse rate, an annuity amount, a settlement option, a deductible amount, a limit or coverage amount, and/or another insurance policy term.

In some cases, a prioritization of different insurance policy terms may be provided. For example, a consumer may require a life insurance policy with a face value of $1,000,000, but may be open to considering a range of premium amounts. Additionally or alternatively, other preferences or requirements relating to insurance, for example, a preference for an insurance company that offers live insurance agents, may be indicated. Generally, any number of preferences and/or requirements (and optionally, respective priorities thereof) for one or more insurance terms, characteristics of insurance policies, and/or characteristics of insurance companies or providers may be indicated (e.g., a priori by the medical diagnostic provider, by the insurance procurer, by one or more of the insurance providers, and/or by the patient or an agent of the patient), and may be used in the selection process.

In some situations, at least a part of the consumer's desired preferences and/or requirements may be received via the computing device 12 and provided to the insurance procurement system 14. For example, the health profiler unit 20, the provider selector unit 22, or some other portion of the system 14 may provide on-line forms as one or more web pages (e.g., HTML files, JavaServer Pages files, etc.) stored in a memory of the insurance procurement system 14, and a user may use web browser applications executing on the computing device 12 to access the web page(s). In some situations, at least a part of the consumer's desired preferences and/or requirements may be obtained during a patient's medical diagnostic examination, and the preferences and/or requirements may be provided by the medical diagnostic provider computing system 34 to the insurance procurement system 14, e.g., in conjunction with the consumer's medical diagnostic examination results.

Whether the consumer's preferences and/or requirements are obtained by the insurance procurement system 14 via the on-line forms, via accessing the examination results database 30 or other data storage entity, and/or via other suitable means, and/or whether the medical diagnostic provider 34 and/or insurance provider 16 preferences and/or requirements are obtained by the insurance procurement system 14 via on-line forms, via accessing the provider database 32 or other data storage entity, via messaging or other communications, and/or via other suitable means, the health profiler unit 20 and/or the provider selector unit 22 of the system 14 may collect or obtain the insurance preferences and/or requirements, and the provider selector unit 22 may utilize the collected insurance preferences and/or requirements to determine or select one or more insurance providers 1-N to which the patient's health profile is to be sent for bid or quote. The determination of patient eligibility (e.g., by the eligibility determiner unit 21) and the determination/selection of the recipient insurance provider computing systems that are to receive the patient's health profile (e.g., by the provider selector unit 22) may be performed sequentially, concurrently, and/or iteratively.

Further, as previously discussed, the selection of recipient insurance providers may be based upon data included in and/or characteristics of the patient's health profile, and/or may be based upon characteristics of the types of insurance products offered by the different insurance providers 1-N. For example, if insurance provider 2 offers life insurance products for diabetics, insurance provider computing system 16-2 would be selected for diabetic patients, as indicated by the data included in the patients' health profiles.

In one embodiment, the characteristics of the types of insurance products offered by the different insurance providers 1-N may be stored in a provider database or data storage entity 32. Additionally or alternatively, the selection of recipient insurance providers may be based upon other criteria that are not related to consumers or patients at all, such as random selection of insurance providers, ordered selection, network and/or insurance provider system 16 availability, etc.

In some embodiments, the provider selector unit 22 of the insurance procurement system 14 may filter the set of possible insurance provider computing systems 16-1 through 16-N, and may send the request for quote to only a subset of the systems 16-1 through 16-N. For example, the insurance procurement system 14 may determine the subset of insurance provider computing systems 16-1 through 16-N to which the health profile of the patient is to be sent based upon one or more preferences for insurance terms, policy characteristics, and/or provider characteristics as indicated by the consumer. In some situations, one or more preferences for insurance terms, insurance providers, and/or other characteristics of insurance policies as indicated by the consumer may be sent or provided with the health profile to each of the selected insurance provider computing systems 16-1 through 16-N.

In some situations, the provider selector unit 22 may be omitted from the system 14, such as when the insurance procurement system 14 is communicatively connected to the computing system(s) of only a single insurance carrier, provider, or company. For example, the system 14 may be communicatively connected to only the computing system 16-N and not to any of the computing systems 16-1 through 16-(N−1). In one embodiment, the entity or organization that owns and/or operates the insurance procurement system 14 may be a subsidiary or business partner of the insurance company N. As such, in situations in which a medical diagnostic provider owns and/or operates the insurance procurement system 14, the medical diagnostic provider may be a subsidiary or other type of business partner of the insurance company N.

Further, at least some or all of the eligibility determiner unit 21 may be included in the health profiler unit 20, the provider selector unit 22, and/or some other unit of the insurance procurement system 14. The eligibility determiner unit 21 may be omitted, such as when all health profiles are automatically sent to one or more insurance providers to 16-1 to 16-N. In some embodiments, the eligibility determiner unit 21 and the provider selector unit 22 are an integral unit.

A policy procurement unit 24 may obtain or procure one or more offers for insurance, e.g., when the patient has been determined to be a potential, eligible insured party. The policy procurement unit 24 may conduct an automated auction in order to obtain insurance policies for the patient, e.g. in a manner similar to that described in U.S. Patent Application No. 62/104,596, filed on Jan. 16, 2015 and whose entire contents are hereby incorporated herein by reference, or in another suitable manner. For example, the policy procurement unit 24 may send or provide, to each of the selected insurance provider computing systems 16-1 through 16-N, the health profile of the patient and/or other selected data indicative of the patient's examination results that are stored in the database 30, along with a request for insurance premium quotes.

After analyzing the information, one or more of the insurance providers may decide to bid on the provision of insurance to the consumer, and/or policy procurement unit 24 may receive the bid(s) from the respective ones of insurance provider computing systems 16-1 through 16-N. Policy procurement unit 24 may send each received bid to all others of the insurance provider computing systems 16-1 through 16-N, and/or bidding may continue in an iterative fashion until auction termination criteria have been met (e.g., until a predetermined amount of time elapses, or until a predetermined amount of time since the last bid elapses, etc.). The insurance provider having the best bid (e.g., lowest price and/or best non-price features) at the time the auction terminates may be granted the ability to provide insurance to the consumer. Typically, the bids of the insurance provider computing systems 16-1 through 16-N may be, or may include, binding quotes or offers for respective insurance policies that have been generated or determined based upon the health profile of the consumer. Accordingly, the terms of the insurance policy corresponding to a binding quote may not change (although a lifetime of the binding quote typically is finite and may be indicated as such), and upon acceptance of the binding quote, a corresponding contract for insurance may be enacted or entered into, by the insurance procurement system 14, on behalf of the consumer.

In another embodiment, the policy procurement unit 24 may obtain the best rate or the most suitable insurance policy for the patient not by conducting an auction, but rather by automatically requesting a single quote from each of the insurance providers, and taking the best quote (e.g., the lowest premium, and/or a quote with other features best matching the consumer's preferences and/or requirements). Similar to the auction embodiments described above, policy procurement unit 24 may automatically request a round of quotes from the insurance providers at when new or updated medical diagnostic exam results of the patient are available. For example, the policy procurement unit 24 may automatically send or provide the health profile of the patient and optionally one or more preferred insurance terms, insurance policy characteristics, and/or insurance provider characteristics as indicated by the patient or consumer to the insurance provider computing systems 16-1 through 16-N. The notification unit 26 may simply notify the consumer of the accepted policy and provider, or may first request confirmation or selection of a particular policy/provider. The presentation of the candidate insurance offers for selection and/or confirmation may be performed electronically, e.g., via a user interface of the computing device 12.

Whether the one or more binding quotes are generated by an auction, by a single bid or quote, or by some other suitable manner, the insurance procurement system 14 may receive, from one or more responding insurance provider computing systems 16-1 to 16-N, one or more binding quotes for offers for insurance. The one or more binding quotes may be for a same type of insurance, and/or may be for different types of insurance. Additionally or alternatively, at least some of the binding quotes may be for a same or similar set of insurance policy terms, and/or at least some of the binding quotes may be for different insurance policy terms. In one embodiment, the notification unit 26 of the insurance procurement system 14 may cause indications of the one or more received binding offers for insurance to be provided to a user, e.g. by presentation at a respective user interface of the systems 12, 14, 34, and/or at least one of 16-1 to 16-N, by email, by physical letter, etc., thereby initiating the one or more offers for the one or more types of insurance for which the patient has been determined to be eligible and that include one or more binding quotes, any one of which may result in a contract for insurance upon its acceptance.

In one embodiment, in response to the insurance offer notifications, the insurance procurement system 14 may receive an indication of a selection of one of the binding quotes, e.g., at a respective user interface of the systems 12, 14, 34, and/or at least one of 16-1 to 16-N, by email, by physical letter, etc. For example, a selection of one of the binding quotes may be provided by the patient and/or by the patient's agent. The insurance procurement system 14 may provide an indication, to the insurance provider computing system 16x of the selected binding quote, that the particular binding quote has been selected. The insurance provider computing system 16x of the selected binding quote may proceed to underwrite, bind, and/or perform other actions to move the insurance policy towards being in force. Further, the insurance provider computing system 16x may provide, to the insurance procurement system 14, one or more indications that one or more of the actions has been completed, e.g., that the policy has been underwritten, that the policy has been bound, that the policy is in-force, etc. Upon reception of one or more indications of rendering actions that have been completed by the insurance provider computing system 16x, the insurance procurement system 14 may refund at least a part of the cost of the medical diagnostic examination, and/or may credit at least a part of the cost of the medical diagnostic examination towards future premiums of the insurance policy.

In some embodiments, the binding quotes or offers for insurance policies that have been generated for the patient are the first offers for insurance that have been generated and brought to the patient's attention that have been generated based upon the patient's recently performed medical diagnostic examination. That is, the patient has no prior knowledge of potential offers for insurance that may be generated based upon his or her medical examination results, and is conveniently provided with one or more binding quotes for insurance for which the patient has already been determined to be eligible as an insured party.

In other embodiments, though, a patient may be aware that his or her examination results will be automatically be analyzed to procure offers for insurance for which the patient is determined to be an eligible insured party. For example, a patient or the patient's agent may provide his or her a priori authorization for the insurance procurement system 14 to enter into a binding contract for a suitable insurance policy on behalf of the patient, with or without some explicit confirmation for election by the patient. If a contract is automatically established by the insurance procurement system 14, the policy procurement unit 24 may indicate to the insurance provider providing the best bid that the best bid has been accepted, and the notification unit 26 may cause the patient or the patient's agent to be informed of the insurance provider and the new policy (e.g., electronically at a user interface of the computing device 12, by email, by physical letter, etc.).

If patient or agent confirmation or selection is required, notification unit 26 may instead cause the patient or agent thereof to be sent an indication of the best offer or offers and the corresponding providers (e.g., electronically at a user interface of the computing device 12, by email, by physical letter, etc.) along with a request for confirmation or selection. Policy procurement unit 24 may then form the contract with the winning insurance provider after the confirmation or selection, for example. In one embodiment, the presentation of the candidate insurance offers for selection and/or confirmation may be performed electronically, e.g., at a user interface of the computing device 12 via a web-browser or client application that has been downloaded to the user device 12 from the procurement system 14.

Thus, as discussed above, in some embodiments, the insurance procurement system 14 may automatically select one of the received quotes on behalf of the patient, e.g., based upon the patient's health profile and one or more preferred insurance terms and/or other characteristics of the insurance provider and/or of the policy. For example, the insurance procurement system 14 may compare the insurance policy terms and/or characteristics of each of the received quotes as part of the selection process, e.g. in light of the patient's health profile, preferences for particular insurance terms, characteristics, and/or providers, if such preferences are available.

In other embodiments, the insurance procurement system 14 may receive the quotes from the insurance provider computing systems 16-1 through 16-N, and may cause multiple quotes to be presented to the patient or other user for selection. In some of these cases, the insurance procurement system 14 may filter the received quotes prior to sending a subset of the received quotes for the consumer's consideration. For example, the insurance procurement system 14 may filter the received quotes based upon one or more preferences for particular insurance terms, insurance policy characteristics, and/or insurance provider characteristics indicated by the patient or the patient's agent, if such preferences are available.

The insurance procurement system 14 may be authorized to enter a binding contract for the policy on behalf of the consumer, or may require some confirmation for election by the consumer. If a contract is automatically established by the insurance procurement system 14, the policy procurement unit 24 may indicate to the insurance provider providing the best bid that the best bid has been accepted, and/or a notification unit 26 may cause the consumer to be informed of the insurance provider and the new policy (e.g., electronically at a user interface of the computing device 12, by email, by physical letter, etc.). If consumer confirmation or selection is required, notification unit 26 may instead cause the consumer to be sent an indication of the best offer or offers and the corresponding providers (e.g., electronically at a user interface of the computing device 12, by email, by physical letter, etc.) along with a request for confirmation or selection. Policy procurement unit 24 may then form the contract with the winning insurance provider after the confirmation or selection, for example. The presentation of the candidate insurance offers for selection and/or confirmation may be performed electronically, e.g., at a user interface of the computing device 12.

In one embodiment, the insurance procurement system 14 may be owned and/or operated by a medical diagnostic provider, such as a physician or other medical professional, a medical diagnostic laboratory (MDL), or other organization providing medical diagnostic examinations to patients. For example, the insurance procurement system 14 may be included in and/or integrated with a computing system 34 that is owned and/or operated by the medical diagnostic provider that performed at least a part of the diagnostic examination of the patient and/or at least part of the results analysis therefrom. Data obtained during the medical diagnostic examination of the patient may be stored (and/or may be analyzed and stored) in the examination results database 30 by other portions of the medical diagnostic provider computing system upon completion of the examination.

In another embodiment, the insurance procurement system 14 may be owned and/or operated by another entity that may not be a medical diagnostic provider, such as by an insurance aggregator, insurance procurer, or other third party organization. In this embodiment, though, the insurance procurement system 14 may nonetheless be communicatively connected to one or more computing systems 34 of one or more medical diagnostic providers, as shown in FIG. 1.

Thus, as the insurance procurement system 14 is configured to automatically initiate or trigger the automatic procurement of insurance coverage on behalf of a patient from the most recent or immediate results of his or her medical diagnostic examination, network traffic within the environment 10 (and indeed, message traffic and resources that are utilized by each of the medical diagnostic provider system 34, the insurance procurement system 14, and at each of the insurance provider systems 16-1 to 16-N) is significantly decreased over known techniques and methods for procuring insurance for the patient. Further, as compared to known techniques and methods, fewer processor cycles and memory records are needed at the medical diagnostic provider system 34, the insurance procurement system 14, and/or at each of the insurance provider systems 16-1 to 16-N to procure insurance for the patient. As such, not only is the patient or consumer saved from needing to initiate the procurement process and provide partial personal information, and is saved from incurring lengthy delays and repetitive actions during the insurance procurement process, but computing system resources and network traffic are also significantly decreased.

Figure 2:
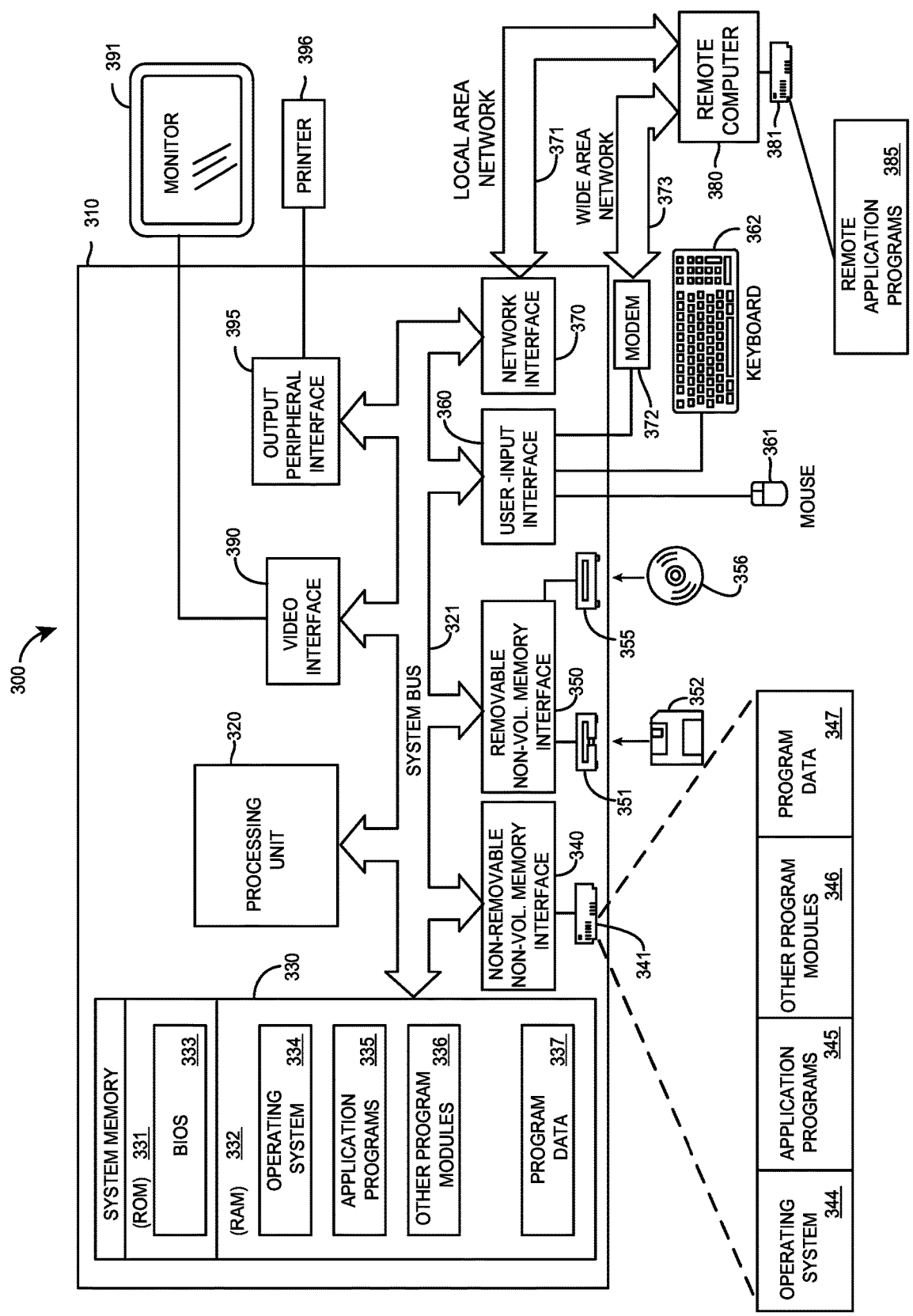
FIG. 2 depicts an exemplary computer system in which the techniques described herein may be implemented, according to one embodiment.

III. Exemplary Computer System for Automatically Initiating Insurance Coverage Based Upon Medical Diagnostic Exams FIG. 2 depicts an exemplary computer system 300 in which the techniques described herein may be implemented. In one embodiment, the computer system 300 may be included in the system 10 of FIG. 1. For example, any one or more of the units 20-26 may comprise one or more instances of the computer system 300, the insurance procurement system 14 may comprise one or more instances of the computer system 300, the medical diagnostic provider system 34 may comprise one or more instances of the computer system 300, and/or each of the insurance provider computing systems 16-1 to 16-N may comprise one or more instances of the computer system 300. The computer system 300 of FIG. 2 may include a computing device in the form of a computer 310. Components of the computer 310 may include, but are not limited to, a processing unit 320, a system memory 330, and/or a system bus 321 that couples various system components including the system memory 330 to the processing unit 320.

The system bus 321 may be any of several types of bus structures including a memory bus or memory controller, a peripheral bus, or a local bus, and may use any suitable bus architecture. By way of example, and not limitation, such architectures include the Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus (also known as Mezzanine bus).

Computer 310 typically may include a variety of computer-readable media. Computer-readable media may be any available media that can be accessed by computer 310 and may include both volatile and nonvolatile media, and both removable and non-removable media. By way of example, and not limitation, computer-readable media may comprise computer storage media and communication media. Computer storage media includes tangible, non-transitory, volatile and nonvolatile, removable and non-removable media implemented in any method or technology for non-transitory storage of information, such as computer-readable instructions, data structures, program modules or other data. Computer storage media may include, but is not limited to, RAM, ROM, EEPROM, FLASH memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by computer 310. Communication media typically embodies computer-readable instructions, data structures, program modules or other data in a modulated data signal, such as a carrier wave or other transport mechanism, and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, radio frequency (RF), infrared and other wireless media. Combinations of any of the above are also included within the scope of computer-readable media.

The system memory 330 may include computer storage media in the form of volatile and/or nonvolatile memory such as read only memory (ROM) 331 and random access memory (RAM) 332. A basic input/output system 333 (BIOS), containing the basic routines that help to transfer information between elements within computer 310, such as during start-up, is typically stored in ROM 331. RAM 332 may typically contain data and/or program modules that are immediately accessible to, and/or presently being operated on, by processing unit 320. By way of example, and not limitation, FIG. 2 illustrates operating system 334, application programs 335, other program modules 336, and program data 337.

The computer 310 may also include other removable/non-removable, volatile/nonvolatile computer storage media. By way of example only, FIG. 2 illustrates a hard disk drive 341 that reads from or writes to non-removable, nonvolatile magnetic media, a persistent memory port 351 that reads from or writes to a removable, nonvolatile persistent memory card or device 352 such as a solid-state drive, a flash drive, a media card, a memory stick, etc., and an optical disk drive 355 that reads from or writes to a removable, nonvolatile optical disk 356 such as a CD ROM or other optical media. Other removable/non-removable, volatile/nonvolatile computer storage media that may be used in the exemplary operating environment include, but are not limited to, magnetic tape cassettes, flash memory cards, digital versatile disks, digital video tape, solid state RAM, solid state ROM, and the like. The hard disk drive 341 may be connected to the system bus 321 through a non-removable memory interface such as interface 340, and persistent memory port 351 and optical disk drive 355 may be connected to the system bus 321 by a removable memory interface, such as interface 350.

The drives and their associated computer storage media discussed above and illustrated in FIG. 2 provide storage of computer-readable instructions, data structures, program modules and other data for the computer 310. In FIG. 2, for example, hard disk drive 341 is illustrated as storing operating system 344, application programs 345, other program modules 346, and program data 347. Note that these components may either be the same as or different from operating system 334, application programs 335, other program modules 336, and program data 337. Operating system 344, application programs 345, other program modules 346, and program data 347 are given different numbers here to illustrate that, at a minimum, they are different copies.

A user may enter commands and information into the computer 310 through input devices such as cursor control device 361 (e.g., a mouse, trackball, touch pad, etc.) and keyboard 362. A monitor 391 or other type of display device is also connected to the system bus 321 via an interface, such as a video interface 390. In addition to the monitor, computers may also include other peripheral output devices such as printer 396, which may be connected through an output peripheral interface 395.

The computer 310 may operate in a networked environment using logical connections to one or more remote computers, such as a remote computer 380. The remote computer 380 may be a personal computer, a server, a router, a network PC, a peer device or other common network node, and typically includes many or all of the elements described above relative to the computer 310, although only a memory storage device 381 has been illustrated in FIG. 2. The logical connections depicted in FIG. 2 include a local area network (LAN) 371 and a wide area network (WAN) 373, but may also include other networks. Such networking environments are commonplace in hospitals, offices, enterprise-wide computer networks, intranets and the Internet.

When used in a LAN networking environment, the computer 310 is connected to the LAN 371 through a network interface or adapter 370. When used in a WAN networking environment, the computer 310 typically includes a modem 372 or other means for establishing communications over the WAN 373, such as the Internet. The modem 372, which may be internal or external and/or wired or wireless, may be connected to the system bus 321 via the input interface 360, or other appropriate mechanism. The communications connections 370, 372, which allow the device to communicate with other devices, are an example of communication media, as discussed above, and may include one or more respective transceivers. In a networked environment, program modules depicted relative to the computer 310, or portions thereof, may be stored in the remote memory storage device 381. By way of example, and not limitation, FIG. 2 illustrates remote application programs 385 as residing on memory device 381.

In some configurations, the computer 310 may be included in a plurality of networked computers or computing devices that have the logical appearance as a single, integral computing node, e.g., a cloud computing system. For example, the application programs 345, other program modules 346 and/or program data 337 may be stored in and executed by the logical, single computing node.

The techniques for automatically initiating insurance coverage based upon completion of medical diagnostic examinations described herein may be implemented in part or in their entirety within a computer system such as the computer system 300 illustrated in FIG. 2. The computer 310 may be a server or computing device of an insurance procurement system (e.g., within the insurance procurement system 14 of FIG. 1), and the remote computer 380 may be a server or computing device of an insurance provider (e.g., within one of the computing systems 16-1 through 16-N of FIG. 1), for example. In some such embodiments, the LAN 371 may be omitted (e.g., communications may between computer 310 and computer 380 may only occur via WAN 373). Application programs 335 and/or application programs 345 may include programs or perspective, particular computer-executable instructions that implement the health profiler unit 20, the eligibility determiner unit 21, the provider selector unit 22, the policy procurement unit 24, and/or the notification unit 26 of FIG. 1, for example. Examination results database 30 and/or provider database 32 may be stored on hard disk drive 341, persistent memory device 352 or optical disk 356, for example. In some embodiments, examination results database 30 and/or provider database 32 may be stored on one or more other data storage devices that are not included in the computer system 300 but nonetheless may be accessible by the computer system 300.

In operation, the computer 310 may receive from the remote computer 380 one or more consumer preferences and/or requirements for any number of insurance terms, insurance policy characteristics, and/or insurance provider characteristics (not shown in FIG. 2), for example, when the remote computer 380 comprises a consumer computing device 12. Further, computer 310 may receive from the remote computer 380 bids, binding quotes, and/or insurance offers (not shown in FIG. 2), for example when the remote computer 380 comprises one or more of the insurance provider computing systems 16-1 through 16-N. The computer 310 may then determine the winning bid and/or the candidate insurance offers, and notify the consumer by sending messages (e.g., emails) to the consumer computing device and/or providing an indication of the winning bid and/or the candidate insurance offers at a user interface of the consumer computing device, for example.

Figure 3:
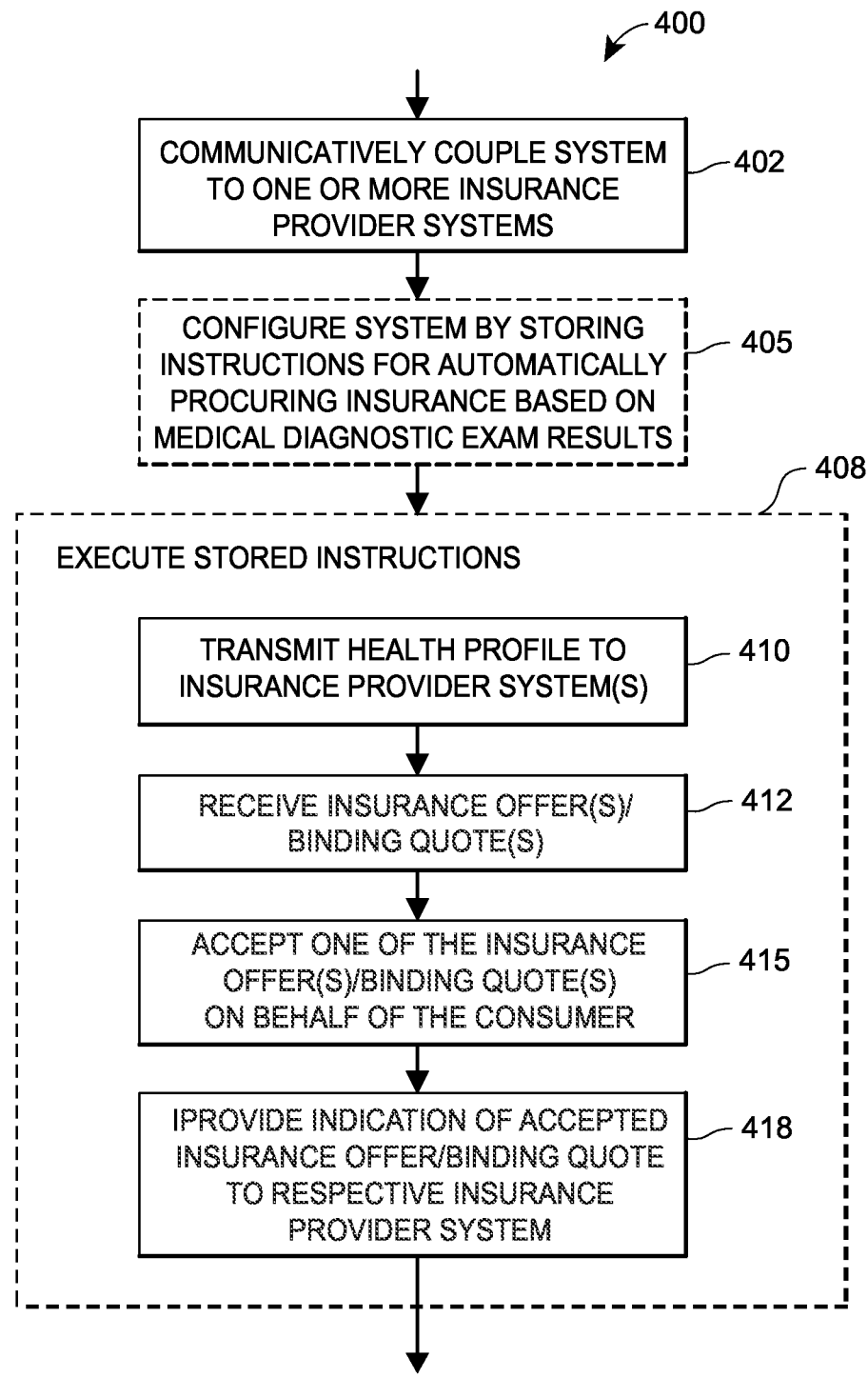
FIG. 3 depicts an exemplary computer-implemented method for providing or initiating procurement of insurance based upon medical diagnostic examinations.

IV. Exemplary Method for Providing or Initiating Procurement of Insurance Based Upon Medical Diagnostic Examinations FIG. 3 illustrates an exemplary method 400 of providing or initiating procurement of insurance based upon completion of medical diagnostic examinations. In one embodiment, at least a portion of the method 400 may be performed by the insurance procurement system 10 of FIG. 1, the medical diagnostic provider system 34, and/or by the computer system 300 of FIG. 2. For example, the method 400 may be performed by executing particular computer-executable instructions stored on the insurance procurement system 14. Indeed, the method 400 may operate in conjunction with the environment 10, the system 14, and/or the system 34 illustrated in FIG. 1, the system 300 of FIG. 2, and/or any one or more portions of any one or more of the other methods described herein.

The method 400 may include, for example, communicatively coupling a system (e.g., the medical diagnostic provider system 34, the insurance procurement system 14, the computer system 300, or another suitable system) to respective computing systems of a plurality of insurance providers (block 402); particularly configuring one or more tangible, non-transitory memories of the system by storing thereon particular computer-executable instructions for initiating procurement of insurance based upon the completion of medical diagnostic examinations and/or the initial availability of corresponding examination results (block 405); and/or executing, by one or more processors of the system, the particular computer-executable instructions (block 408).

In one embodiment, the execution of the particular computer-executable instructions (block 408) may cause the system, after receiving patient permission, to perform transmitting a health profile of a patient to one or more insurance provider computing systems (block 410); receiving one or more insurance offers for one or more insurance policies for which the patient has been determined to be an eligible or approved insured party (block 412); accepting, on behalf of the patient or consumer, one of the one or more insurance offers (block 415); and/or providing an indication of the accepted insurance offer to the particular insurance provider computing system that generated the accepted insurance offer (block 418), thereby entering into a contract for insurance on behalf of the consumer.

The method may include additional, fewer, or alternate actions, including those discussed elsewhere herein. For example, in some embodiments, the blocks 405 and 408 are at least partially omitted, for example, when one or more of the blocks 410-418 are performed by hardware, firmware, and/or any other suitable means for implementing the health profiler unit 20, the eligibility determiner unit 21, the provider selector unit 22, the policy procurement unit 24, and/or the notification unit 26.

Specifically, the method 400 may include communicatively coupling a system to respective computing systems of one or more insurance providers (block 402). For example, the system may be the insurance procurement system 14 of FIG. 1, and the system 14 may be communicatively coupled to insurance provider computing systems 16-1 through 16-N. The system may be coupled to one or more insurance provider computing systems by using any number of any types of communication connections, e.g., direct connections, indirect or staged connections, wired, wireless, etc. In some embodiments, the system may be communicatively coupled to one or more insurance provider computing systems via one or more electronic or communications networks, e.g., wired communication networks, wireless communication networks, local networks, remote networks, public networks, private networks, secured networks, unsecured networks, etc. Typically, the system may include one or more network interfaces that are utilized for the communicative coupling. Further, the system may be communicatively coupled to different insurance provider computing systems 16-1 through 16-N via different network interfaces, connections, and/or networks.

In some embodiments, the system may be owned and/or operated by a medical diagnostic examination provider, and accordingly the system may be a medical diagnostic provider computing system (e.g., referring to FIG. 1, the system 14 and the system 34 may be an integral system). In other embodiments, the system may not be a medical diagnostic provider computing system 34, but nonetheless may be communicatively coupled to a medical diagnostic computing system (e.g., referring to FIG. 1, the system 14 and the medical diagnostic computing system 34 may be separate but communicatively coupled systems).

The method 400 may include particularly configuring one or more tangible, non-transitory memories of the system by storing thereon particular computer-executable instructions for providing or initiating procurement of insurance based upon completion of medical diagnostic examinations (block 405). Referring to FIG. 2 as an illustrative but non-limiting example, the particular computer-executable instructions may be included in the application programs 335 stored on the RAM 332 and/or in the application programs 345 stored on the hard disk drive 341, thereby particularly configuring the computing system 300. The particular computer-executable instructions may have been downloaded or otherwise transferred to the computing system 300, such as via a network interface 370, the persistent memory port 351, or the optical disk port 355, for example.

Further, the method 400 may include executing, by one or more processors of the system, the particular computer-executable instructions (block 408) that are stored in the system. The execution of the particular computer-executable instructions (block 408) may cause the system to automatically initiate the provision or procurement of insurance based upon the completion of medical diagnostic examinations and/or the initial availability and/or storage of examination results, e.g., into the examination results database 30. For example, a medical diagnostic examination may be performed on a patient by a medical diagnostic provider, a physician or other medical professional, a medical diagnostic laboratory, or the like, and at least some of the results of the performed examination may be stored into examination results database 30. Typically, the medical diagnostic examination may include at least one invasive procedure, such as a blood draw and analysis. A health profile of the patient may be determined based upon at least some of the results of the performed examination. Indeed, in one embodiment, the method 400 may include determining the health profile of the patient based upon at least part of the results of the performed medical diagnostic examination (not shown in FIG. 3).

In some embodiments of the method 400 (not shown), the method 400 may include causing the storing of at least some of the results of the patient's medical diagnostic examination (or portions thereof) at the system, e.g., in the examination results data storage device 30. For example, if the system is a computing system 34 of the medical diagnostic provider performing the examination of the patient, the results of the patient's examination may be directly entered and stored into the examination database 30 as the results are determined (that is, the examination database 30 stores original examination results or source copies thereof). On the other hand, if the system is not a medical diagnostic provider computing system 34, but is communicatively coupled to a computing system 34 of the medical diagnostic provider that performed the examination of the patient, the system may receive the patient's examination results or portions thereof from the medical diagnostic provider computing system 34, and upon the receipt of the results at the system, the system may store the patient's examination results or portions thereof into the examination database 30 (that is, the examination database 30 may store duplicate or shadow copies of examination results or portions thereof). At any rate, in some embodiments of the method 400 (not shown), the storage of the patient's medical diagnostic examination results in the examination database 30 may trigger or initiate the system to generate the patient's health profile. For example, the system may aggregate, average, and/or otherwise combine data from the stored, medical diagnostic exam results of the patient to generate the patient's health profile.

In one embodiment, the method 400 may include auctioning a health profile of a patient to procure insurance. The auctioning of the patient's health profile may be similar to the auctioning process described in the aforementioned U.S. Patent Application No. 62/104,596 (which is incorporated herein by reference in its entirety), in one embodiment. For example, auctioning the health profile of the patient may include transmitting or providing the health profile of the patient to recipient insurance provider computing systems included in the plurality of insurance provider computing systems to which the system is communicatively coupled (block 410). The transmission of the health profile of the patient may be performed based upon an indication that the patient or consumer has assented to doing so. For example, an affirmative assent of the patient or consumer may include an indication of permission to release the patient's medical information, and/or a waiver of privacy to the patient's medical information. In some scenarios, the assent of the patient or consumer (or of his or her agent) may be obtained a priori, e.g., when the patient undergoes his or her medical diagnostic examination or at some time prior to the availability of the examination results. An indication of the granted permission and/or waiver may be stored at the system or otherwise indicated to the system.

In some embodiments (not illustrated), prior to transmitting the health profile of the patient thereto (block 410), the method 400 may include determining or selecting recipient insurance provider computing systems. Referring to FIG. 1 as an illustrative but non-limiting example, the system 14 may determine or select which of the insurance provider computing systems 16-1 through 16-N is or are to receive the patient's health profile, e.g., for bidding purposes. The determination or selection of recipient insurance provider computing systems may be based upon, for example, one or more insurance preferences and/or requirements indicated by the consumer or patient, one or more characteristics of the insurance providers 1-N (e.g., as indicated by the provider database 32), an availability of each of the insurance provider computing systems 16-1 through 16-N, and/or other criteria.

Auctioning the patient's health profile (such as via an online auction, or other auction implemented via an electronics or communications network or via wired or wireless data transmission) may include receiving one or more insurance offers (block 412), e.g., from one or more of the recipient insurance provider systems. The one or more insurance offers may correspond to one or more insurance policies for one or more types of insurance that require a medical diagnostic examination to be performed on a potential insured party (e.g., life, health, disability, etc.), and the responding recipient insurance provider computing systems may have determined that the patient is an eligible and/or approved insured party of each of the one or more insurance policies, e.g., based upon the contents of the patient's health profile. As such, the one or more insurance offers may be binding quotes or binding offers for insurance, rather than mere estimates or non-binding quotes or offers.

In some cases, the one or more insurance offers may have been determined by the responding recipient insurance provider computing systems based additionally upon one or more insurance preferences and/or requirements, e.g., as indicated by the patient or consumer, by the system, and/or by the respective, responding insurance provider computing system. For example, an indication of one or more insurance preferences and/or requirements of the patient or consumer may have been transmitted with the patient's health profile to the plurality of insurance provider computing systems (block 410), and at least one of the responding insurance provider computing systems may have generated one or more insurance offers based upon both the patient's health profile and the received insurance preferences and/or requirements.

Moreover, the initial generation of one or more insurance offers for the patient or consumer at respective insurance provider computing systems may have been initially triggered by the reception of the patient's health profile (and optionally of indicated insurance preferences and/or requirements) at the respective insurance provider computing systems, so that the one or more insurance offers are initial sets of insurance offers that are generated by the respective insurance provider computing systems for the patient. For example, a specific responding insurance provider computing system may not initiate or begin generating an insurance offer for the patient or consumer until the patient's health profile is received at the specific responding insurance provider computing system from the system (e.g., from the insurance procurement system 14 or from the computing system 300). That is, the respective insurance provider computing system does not receive (from the system 14, the system 300, any other system, or any user interface) any partial personal information corresponding to the patient and relating to the generation of the one or more insurance offers prior to receiving the patient's health profile from the system (e.g., from the system 14 or the system 300). Indeed, in some cases, the patient's health profile may be the only indication of a quality of health of the patient that is received by the respective insurance provider computing system corresponding to the offers for insurance, and/or the one or more insurance offers may be generated from the only indication of the patient's quality of health.

Auctioning the patient's health profile may include comparing the received plurality of insurance offers (not shown).

For example, the system may compare the received plurality of insurance offers based upon one or more insurance preferences and/or requirements indicated by the patient or consumer, and/or optionally based upon a prioritization of the preferences and/or requirements indicated by the patient or consumer. If the patient or consumer has not indicated any insurance preferences and/or requirements, the system may compare the received plurality of insurance offers based upon one or more default criteria, e.g., the lowest monthly premium amount.

Auctioning the patient's health profile may include accepting, on behalf of the patient or consumer, one of the received plurality of insurance offers (block 415). For example, the system may receive an indication of the consumer's preferences, requirements, and/or priorities of one or more insurance characteristics, and the system may automatically select the one of the plurality of insurance offers that best meets the preferences, requirements and/or priorities of the consumer (or alternatively, that best meets the one or more default criteria). The system may automatically accept the selected insurance offer on behalf of the consumer, for example, when permission or authorization for the system to automatically select and/or accept insurance offers has been granted by the consumer or his or her agent a priori.

In one embodiment, permission or authorization for the system to automatically select and/or accept a suitable insurance offer on behalf of the consumer may have been provided by the consumer, for example, in conjunction with the consumer granting permission to release his or her medical information, and/or with providing a waiver of privacy to the patient's medical information. In some scenarios, the permission or authorization for selecting and/or accepting an insurance offer on behalf of the consumer or patient may be obtained when the patient undergoes his or her medical diagnostic examination, and/or an indication of the granted permission or authorization may be stored at the system or otherwise indicated to the system.

At a block 418, the method 400 may include providing, by the system, an indication of the selected insurance offer to the particular insurance provider computing system from which the offer was received, thereby entering into a contract for insurance on behalf of the patient or consumer. The receipt of the indication of the selected offer may cause the particular insurance provider computing system to initiate binding of the insurance offer, for example.

In one embodiment, after binding has been completed, the particular insurance computing system may return to the system an indication that the selected insurance offer has been bound (not shown). Upon reception of the indication, the system may cause the patient or consumer to be informed that the insurance offer has been bound, and therefore his or her insurance policy is established or in-force. For example, the system may cause an indication that the insurance offer has been bound to be presented to the consumer, e.g., at the computing device 12 or other user interface. Additionally or alternatively, the system may cause an indication of the bound insurance to be stored, e.g., in the provider database 32 or in some other data storage entity that is included in, accessible to, and/or communicatively connected to the insurance procurement system.

In some embodiments (not shown), upon reception of the indication that the insurance offer has been bound, the system may cause at least a portion of the cost of performing the medical diagnostic examination to be reimbursed. For example, the system may cause the generation of a refund of at least a portion of the cost of the examination, or the system may cause a credit corresponding to at least a portion of the cost of the examination to be credited towards a future premium of the insurance policy.

While the method 400 has been described above with respect to a particular patient's health profile, this is only one of many embodiments. For example, a particular patient's health profile may be grouped with the health profiles of other patients, and the group of health profiles may be auctioned to various insurance providers and at least some of the insurance providers may return one or more bids for the group of health profiles, e.g., in a manner such as described in aforementioned U.S. Patent Application No. 62/104,596 (which is incorporated herein by reference in its entirety). Indeed, any one or more of the techniques described herein for initiating the procurement of insurance based upon medical diagnostic examinations may operate in conjunction with one or more aspects of U.S. Patent Application No. 62/104,596, if desired.

Figure 4:
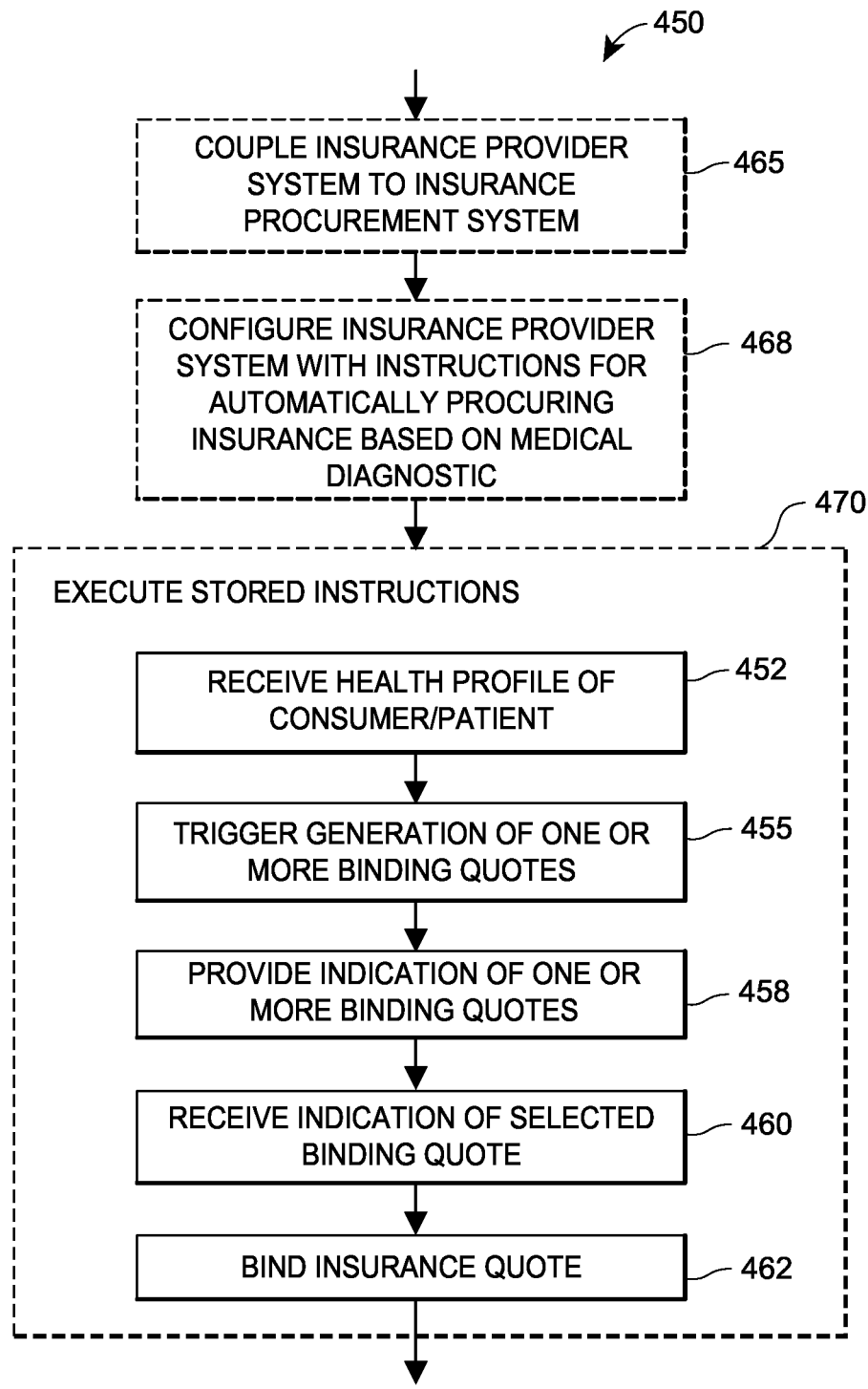
FIG. 4 depicts an exemplary computer-implemented method for providing or procuring insurance based upon medical diagnostic examinations.

V. Exemplary Method for Providing or Initiating Procurement of Insurance Based Upon Medical Diagnostic Examinations FIG. 4 illustrates an exemplary computer-implemented method 450 of automatically providing or procuring insurance based upon medical diagnostic examinations, e.g. based upon their completion and/or on the initial availability of their results. That is, FIG. 4 illustrates an exemplary computer-implemented method 450 of providing insurance triggered by medical diagnostic examinations, e.g. via an electronic or communications network. In one embodiment, at least a portion of the method 450 may be performed by the insurance procurement system 14 of FIG. 1, the medical diagnostic provider system 34, and/or by the computer system 300 of FIG. 2. In one exemplary embodiment, though, at least a portion of the method 450 may be performed by one or more of the insurance provider computing systems 16-1 to 16-N of FIG. 1. For example, the method 450 may be performed by executing particular computer-executable instructions stored on the one or more of the insurance provider computing systems 16-1 to 16-N. Indeed, the method 450 may operate in conjunction with the environment 10, the system 14, and/or the system 34 illustrated in FIG. 1, the system 300 of FIG. 2, and/or any one or more portions of the other methods described herein.

The method 450 may include, in one embodiment, receiving a health profile of a patient, customer, or consumer (block 452), where the health profile has been generated based upon at least a portion of the results of a medical diagnostic examination performed on the patient; triggering, based upon the contents of the patient's health profile, the generation of one or more binding insurance offers or binding quotes for insurance policies for which the patient is an eligible and/or approved party 455; providing, an indication of the one or more binding quotes for insurance 458; receiving an indication that one of the binding quotes for insurance has been selected 460; and/or binding the selected insurance quote 462. The method may include additional, fewer, or alternate actions, including those discussed elsewhere herein.

For example, in one embodiment, at least portions of the method 450 may be performed by one or more of the insurance provider systems 16-1 to 16-N. As such, in this embodiment, the method 450 may include communicatively coupling the system 16-x (e.g., one or more of the systems 16-1 to 16-N) to an insurance procurement system (block 465), such as the insurance procurement system 14 of FIG.

1. The system 16-*x* may be coupled to the insurance procurement system by using any number of any types of electronic or communication connections, e.g., direct connections, indirect or staged connections, wired, wireless, etc. In some embodiments, the system 16-*x* may be communicatively coupled to the insurance procurement system via one or more electronic or communications networks, e.g., wired communication networks, wireless communication networks, local networks, remote networks, public networks, private networks, secured networks, unsecured networks, etc. Typically, the system 16-*x* may include one or more network interfaces that are utilized for the communicative coupling. Further, the system 16-*x* may be communicatively coupled to one or more medical diagnostic provider system 34, such as when the insurance procurement system 14 and the medical diagnostic provider system 34 are an integral system.

In one embodiment, the method 450 may include particularly configuring one or more tangible, non-transitory memories of the system 16-*x* by storing thereon particular computer-executable instructions for procuring insurance based upon medical diagnostic examinations (block 468). Referring to FIG. 2 as an illustrative but non-limiting example, the particular computer-executable instructions may be included in the application programs 335 stored on the RAM 332 and/or in the application programs 345 stored on the hard disk drive 341, thereby particularly configuring the computing system 300. The particular computer-executable instructions may have been downloaded or otherwise transferred to the computing system 300, such as via a network interface 370, the persistent memory port 351, or the optical disk port 355, for example.

The method 450 may include executing, by one or more processors of the system 16-*x*, the particular computer-executable instructions (block 470), e.g., the instructions stored in and particularly configuring the system 16-*x*. The execution of the particular computer-executable instructions (block 470) may cause automatic procurement of insurance based upon the availability of medical diagnostic examination results. For example, the execution of the particular computer-executable instructions may cause the system 16-*x* to perform one or more of the blocks 452-462 of the method 450, and/or optionally one or more other steps. In some embodiments, the block 468 and/or the block 470 are at least partially omitted, such as when at least a portion of at least some of the blocks 452-462 are performed by hardware and/or firmware.

Turning to block 452, in one embodiment, the method 450 may include receiving a health profile of a patient, consumer, customer, or subject on which a medical diagnostic examination has been performed, e.g., by a medical diagnostic provider, a physician or other medical professional, a medical diagnostic laboratory, or the like (block 452). As previously discussed, typically, the medical diagnostic examination may have included at least one invasive procedure, such as a blood draw and analysis, and in some scenarios, the medical diagnostic examination may have been performed as part of the patient's annual physical examination. Some or all of the examination results may have been used to determine and/or generate the received health profile, e.g., as previously discussed above.

For example, at least a portion of the results of the medical diagnostic examination of the patient may have been received by the insurance procurement system 14, the insurance procurement system 14 may have generated the health profile therefrom, and the health profile may have been received at the insurance provider system 16-*x* from the insurance procurement system 14 (e.g., via a network interface coupling the insurance provider system 16-*x* to an electronic or communications network and the insurance procurement system 14). In one embodiment, the patient's health profile is received (block 452) as part of an auction, e.g., as part of an online auction performed by the system 14, such as previously described, and as such, the insurance provider system receiving the patient's health profile (block 452) is one of a plurality of insurance provider systems to which the patient's health profile may be provided. In another example, the patient's health profile may be received by the insurance provider system 16-*x* from the medical diagnostic provider computing system 34.

Upon receiving the patient's health profile (block 452), the method 450 may include triggering, based upon the contents of the health profile, the initial generation of one or more binding quotes for one or more insurance policies for which the patient is eligible to be an insured party (block 455), where the one or more insurance policies are one or more types of insurance that require a medical diagnostic examination to be performed on a potential insured party, e.g., life insurance, long-term care insurance, health insurance, disability insurance, etc. For example, one or more processors of the insurance provider system 16-*x* may trigger the initial generation of the one or more binding quotes based upon the contents of health profile of the patient. The binding quotes whose generation is triggered at the block 455 are initial or first quotes generated by the insurance provider system 16-*x* for the patient, as the generated binding quotes are the first, initial, or only estimates or quotes for insurance that are generated by the recipient insurance provider computing device 16-*x* based upon the particular patient examination results that have been received (block 452). That is, prior to the execution of the block 458, no other estimates, ball-park quotes, non-binding quotes, and/or binding quotes for insurance have been generated by the recipient insurance provider system 16-*x* based upon the received health profile, or indeed, based upon the patient's medical diagnostic examination results from which the patient's health profile was generated.

Furthermore, with regard to the recipient insurance provider system 16-*x*, the health profile of the patient may be the only received indication of a quality of a health of the patient corresponding to the one or more binding quotes. For example, none of the binding quotes are generated at the block 455 based upon any information corresponding to the patient and received at the recipient insurance provider system prior to the receipt of the patient's health profile.

In one embodiment, triggering the initial generation of the one or more binding quotes (block 455) may include generating at least one of the one or more binding quotes, where the one or more binding quotes are an initial and only set of quotes for insurance that are generated for the patient. Furthermore, in some cases, the one or more initial binding quotes may be generated based additionally upon one or more insurance policy term/parameter preferences and/or requirements, e.g., as indicated by the patient or consumer, an agent of the patient or consumer, and/or as indicated by one or more of the systems 34, 14 and/or 16-*x*. For example, an indication of one or more insurance term/parameter preferences and/or requirements of the patient or consumer may have been received in conjunction with the patient's health profile (block 452). The one or more insurance preferences and/or requirements of the patient or consumer may include, for example, one or more preferred insurance policy terms such as an amount of a premium payment, a length of term, a type of insurance, a payout amount, an annuity amount, a settlement option, and/or another insurance policy term or parameter.

In one embodiment, the method 450 may include providing an indication of one or more of the generated binding quotes (block 458) to another computing system, to one or more user interfaces, to a database or data storage entity (e.g., the data storage entity 32), etc. For example, the insurance provider system 16-*x* may provide an indication of one or more of the generated binding quotes to the recipient computing system(s) and/or user interfaces via the network interface coupling the insurance provider system 16-*x* to the electronic or communications network. If more than one binding quote was generated (block 455), an indication of each generated binding quote may be provided (block 458).

Additionally, the method 450 may include receiving an indication that one of the generated binding quotes has been selected (block 460). For example, one of the plurality of binding quotes may have been automatically been selected by the insurance procurement system 14 as part of an auction, or the patient or patient's agent may have selected one of the plurality of binding quotes. For example, the indication of the binding quote selection may be received at the insurance provider system 16-*x* via the network interface and the electronic or communications network from a computing system or user interface to which the plurality of binding quotes was provided (block 458).

At a block 462, the method 450 may include binding the selected insurance quote, where the bound, selected binding quote is for a particular insurance policy for which the patient is named as an insured party. For example, the one or processors of the insurance provider system 16-*x* may bind the selected insurance quote, thereby procuring insurance and/or establishing an in-force insurance policy for the patient. Binding the insurance quote (block 462) may include entering into a contract for insurance with the patient or consumer. The selected insurance offer may be automatically bound on behalf of the patient or consumer, for example, when permission or authorization for the system to automatically select and/or accept insurance offers has been granted by the patient or consumer. Typically, the consumer's permission or authorization has been provided a priori, e.g., in a manner such as previously discussed.

In one embodiment, the method 450 may include causing underwriting to be performed on one or more binding quotes. For example, generating the one or more binding quotes (block 455) may include underwriting at least some of the one or more binding quotes, and/or binding the selected insurance quote (block 462) may include causing underwriting to be performed on the selected binding quote. The one or more processors of the insurance provider system 16-*x* because the underwriting to be formed on the one or more binding quotes.

After binding has been completed (block 462), the method 450 may include providing an indication that the selected insurance quote has been bound (not shown), e.g., to the system from which the patient's health profile was received, to one or more user interfaces, to a database or data storage entity (e.g., the data storage entity 32), etc. via the network interface and the electronic or communications network. Upon reception of the indication, the entity receiving the indication of the bound insurance policy may cause the patient or consumer to be informed that the insurance offer has been bound, and that a contract for insurance has been entered into on behalf of the patient or consumer. For example, the receiving entity may cause an indication that the insurance offer has been bound to be presented to the consumer, e.g., at the computing device 12 or other user interface.

In some embodiments, upon reception of the indication that the insurance offer has been bound, the receiving entity may cause at least a portion of the cost of performing the medical diagnostic examination to be reimbursed. For example, the receiving entity may cause the generation of a refund of at least a portion of the cost of the examination, or the receiving entity may cause a credit corresponding to at least a portion of the cost of the examination to be credited towards a future premium of the insurance policy.

While the method 450 has been described above with respect to a particular patient's health profile, this is only one of many embodiments. For example, a particular patient's health profile may be grouped with the health profiles of other patients, and the group of health profiles may be received at an insurance provider system 16-*x* as part of an auctioning process, in which more than one insurance provider returns one or more bids for the group of health profiles, e.g., in a manner such as described in aforementioned U.S. Patent Application No. 62/104,596. Indeed, any one or more of the techniques described herein for initiating the procurement of insurance based upon medical diagnostic examinations may operate in conjunction with one or more aspects of U.S. Patent Application No. 62/104,596, if desired.

VI. Exemplary Insurance-Based Embodiments

To solve the problem of requiring the customer submit partial personal information without knowing if he or she is actually medically eligible for an insurance policy, an insurance provider may start a subsidiary or partner with a firm that specializes in medical diagnostics, e.g., a medical diagnostic provider or medical diagnostic laboratory (MDL). In this case, the customer who is looking for insurance coverage may make an appointment with the medical diagnostic provider or lab to conduct the diagnostic examination to determine the customer's health profile or present health. The customer may use cash, credit or a debit card, or any other form of payment to cover the cost of the medical diagnostic exam. After the results of the exam are completed and available, the subsidiary or partner, acting on the customer's behalf (and with the customer's permission), may initiate an online or other auction with insurance carriers to find the carrier that may offer the customer, based upon the customer's medical diagnostic exam results, the best premium payment or other feature(s) to meet the customer's insurance need. After the insurance policy is booked, the insurance carrier may either refund the customer for the price of the medical diagnostic exam or credit this amount towards the customer's first insurance premium payment.

Figure 5:
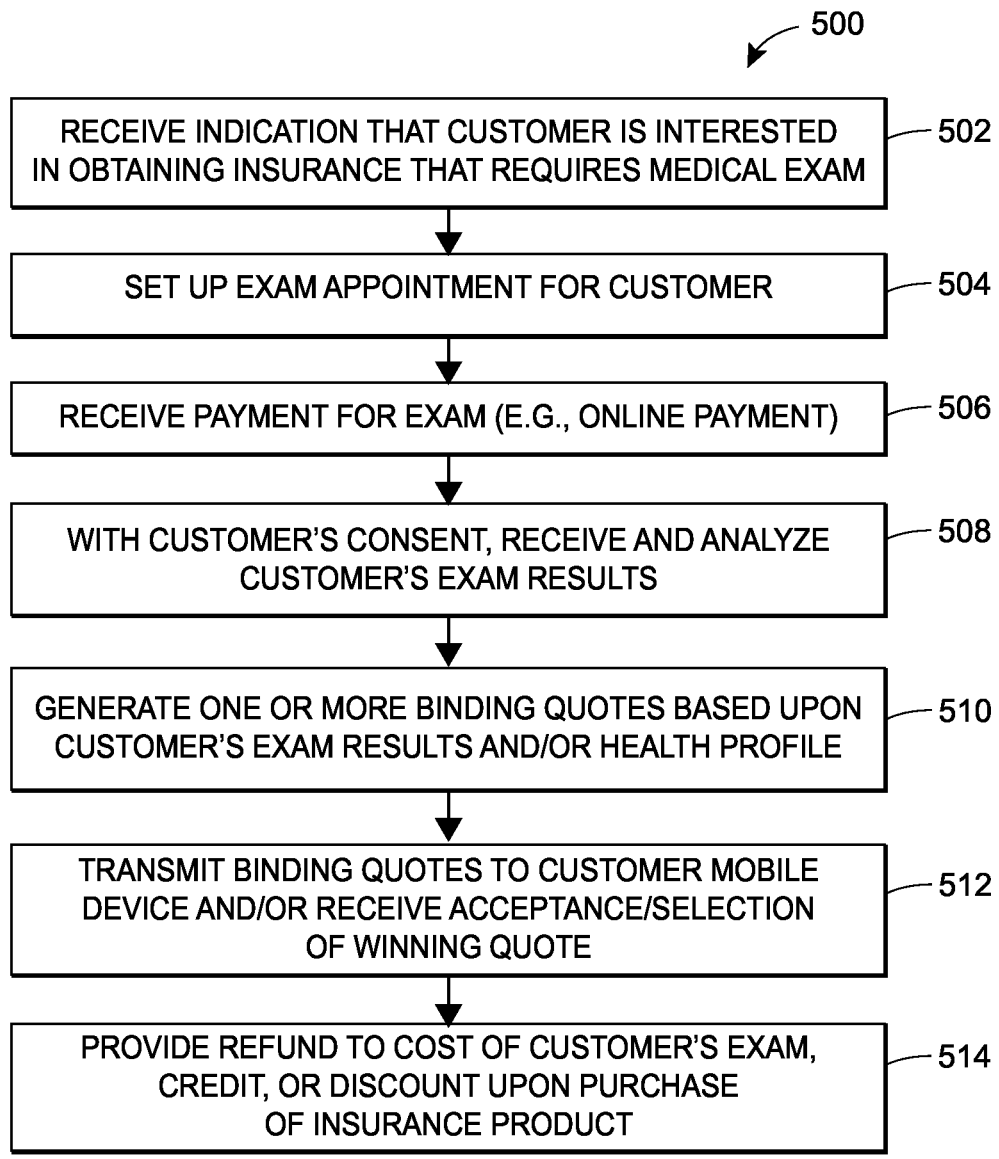
FIGS. 5 and 6 depict additional exemplary computer-implemented methods for providing or procuring insurance based upon medical diagnostic examinations, and providing refunds of medical diagnostic provider or laboratory (MDL) exam costs to health-related insurance policy customers.

FIG. 5 depicts an exemplary computer-implemented method of providing or procuring insurance (e.g., a bound insurance product) to an on-line customer 500. The method 500 may be utilized for providing or procuring insurance via an electronic or communications network and based upon customers' medical diagnostic examinations, for example. One or more portions of the method 500 may operate in conjunction with the systems 14, 34, and/or 16-1 to 16N of FIG. 1, the system 300 of FIG. 2, and/or with any one or more portions of the other methods described herein. For example, at least a portion of the method 500 may be executed by one or more processors of the insurance procurement system 14, e.g., by using one or more electronic or communications networks. Additionally or alternatively, at least a portion of the method 500 may be executed by one or more processes of the medical diagnostic provider system 34, e.g., by using one or more electronic or communications networks.

It is noted that although the method 500 is discussed below with simultaneous reference to FIGS. 1-3, this is merely for ease of discussion, and is not limiting in any way. Generally, the method 500 may be applicable for any number of any types of insurance that require a medical diagnostic examination to be performed on a potential insured party, e.g., life insurance, health insurance, disability insurance, long-term care insurance, etc., but may be equally applicable to other types of insurance, e.g., automobile insurance, personal liability insurance, etc.

The method 500 may include receiving an indication that a customer is interested in purchasing insurance 502; setting up an appointment for the customer with the medical diagnostic provider for a medical diagnostic exam 504; receiving payment from the customer for the medical diagnostic exam 506; receiving and analyzing results from the medical diagnostic exam with the customer's consent 508; generating one or more binding quotes for insurance (and/or a health profile) based upon medical diagnostic exam results 510; transmitting the one or more binding quotes for insurance to the customer and/or receiving acceptance and/or selection of a quote or winning bid 512; and/or refunding the cost of the medical diagnostic exam to the customer upon purchase of the insurance product 514. The method may include additional, less, or alternate actions, including those discussed herein, and/or may be implemented via one or more processors or servers (such as processors or servers associated with insurance providers, medical diagnostic providers, customers (such as customer mobile devices), insurance lead aggregators, and/or others), electronic or communications networks, and/or computer-executable instructions stored on non-transitory, computer-readable media or medium. In one embodiment, a system provides a client application that executes on a customer's device 12, and the client application and the system operate in conjunction to perform the method.

The method 500 may include receiving an indication that an on-line customer is interested in purchasing insurance 502. For instance, medical diagnostic provider or insurance provider remote server may receive an electronic indication that a customer is interested in insurance, such as receiving a transmission or request for information from a website and/or via the customer's mobile device or other computing device 12. The insurance may be of any type or types of insurance that requires a potential insured party to undergo a medical diagnostic examination, the results of which are used to determine insurance policy terms. Examples of such types of insurance include insurance (e.g., term, whole life, universal life, etc.), disability insurance, long-term care insurance, health insurance, etc.

In one embodiment, upon receiving the indication from the customer 502, the system may cause a client application to be downloaded to a client computing device 12, and the client application executes in conjunction with the system to procure insurance for the customer. In another embodiment, the client computing device 12 executes a web-browser or web-based application that executes in conjunction with the system to procure insurance for the customer.

The method 500 may include setting up or scheduling an appointment for the customer with the medical diagnostic provider for a medical diagnostic exam 504. For instance, the processors of the medical diagnostic provider system 34 and/or the insurance provider system 14 may check available time slots for a medical diagnostic exam appointment, and provide one or more options (or exam time slots) for the customer to accept, such as accept via their mobile device 12.

The method 500 may include receiving payment from the customer for the medical diagnostic exam 506. For instance, electronic payment for the medical diagnostic exam may be received via payment from a credit card or checking account over the Internet or other wired or wireless communication networks.

The method 500 may include receiving and analyzing results from the medical diagnostic exam with the customer's consent 508. For example, after the customer provides affirmative consent to release his or her medical information, the medical diagnostic exam results of a portion thereof may be received, e.g. via one or more electronic or communications networks by one or more processors (or servers) from the medical diagnostic provider system 34. Upon receipt of the customer's medical diagnostic examination results, one or more processors associated with the medical diagnostic provider 34, the insurance procurement system 14, and/or the insurance provider(s) 16-1 to 16-N may analyze the received results. In one embodiment, a health profile of the customer may be generated from the analysis of the customer's exam results.

The method 500 may include generating one or more binding quotes for insurance (and/or a health profile) based upon medical diagnostic exam results 510. In one embodiment, a single insurance provider may analyze the medical diagnostic exam results and generate a binding quote for life and/or other types of insurance for the customer. In another embodiment, the system (e.g. the medical diagnostic system 34 and/or the insurance procurement system 14) may generate a health profile of the customer, and the health profile may be provided to numerous insurance providers.

Subsequently, the system (e.g., the medical diagnostic system 34 or the insurance procurement system 14) may receive several binding quotes from the numerous insurance providers. For example, an online auction of the opportunity to provide insurance to the customer (which may result in several binding quotes, or even a single winning quote), may be performed electronically via wired or wireless communication and/or data transmission, e.g., by transmitting the customer's health profile and/or at least a portion of the customer's medical diagnostic exam results to various insurance provider system 16-1 to 16-N. In one embodiment, generating the one or more binding quotes for insurance may include generating the quotes based upon one or more preferred insurance policy terms, such as an amount of a premium payment, a term length, an insurance provider rating, a desired type of insurance, a payout amount, an annuity amount, a settlement option, or one or more other insurance policy terms. At least one of the preferred insurance policy terms may be indicated by or received from the customer, for example, e.g., from his or her mobile computing device 12.

The method 500 may include transmitting the one or more binding quotes for insurance to the customer and/or receiving acceptance and/or selection of a quote or winning bid 512. For instance, the binding quote or quotes may be transmitted to a client application or a browser application executing on the customer's mobile device 12 via one or more electronic indications networks. The customer may then accept one of the binding quotes to have a bound insurance product provided by the insurance provider, and as such, the method 500 may include receiving, from the customer's mobile device 12, an indication of an acceptance and/or a selection of a particular binding quote.

The method 500 may include, upon a purchase of insurance product corresponding to the particular binding quote, electronically refunding at least a portion of the cost of the medical diagnostic exam to the customer upon purchase of the insurance product, electronically crediting an account of the customer, and/or providing a discount to the customer (reference 514). For instance, the insurance provider system 16-1 to 16-N, the insurance procurement system 14, and/or the medical diagnostic provider system 34 may electronically refund the cost of the medical diagnostic exam to the customer's bank or credit card account after the customer has purchased a bound insurance product.

In one embodiment, the method 500 may further include transmitting an indication that an insurance policy corresponding to the particular binding quote has been bound (not shown), and as such the procured insurance policy has been established or is in-force. For example, such an indication may be transmitted to the customer's mobile device 12 via one or more electronic or communications networks.

In one aspect, a computer-implemented method of providing a bound insurance product to an online customer may be provided. The method may include (1) receiving, via one or more processors (such as a medical diagnostic provider or insurance provider remote processor or server), an electronic indication that a customer is interested in purchasing insurance (such as via wired or wireless communication and/or data transmission); (2) scheduling or setting up, via one or more processors, an appointment for the customer interested in purchasing insurance with the medical diagnostic provider for a medical diagnostic exam; (3) receiving, via one or more processors, electronic payment from the customer for the medical diagnostic exam; (4) receiving and analyzing results from the medical diagnostic exam, via one or more processors, with the customer's consent (such as via wired or wireless communication and/or data transmission); (5) generating one or more binding quotes for insurance (and/or a health profile) based upon medical diagnostic exam results, via one or more processors; (6) transmitting, under the direction and/or control of one or more processors (and/or a related transceiver), the one or more binding quotes for insurance to the customer's mobile device (such as via wireless communication and/or data transmission); (7) receiving acceptance and/or selection of a quote or winning bid, via one or more processors (and/or a related transceiver) from the customer's mobile device (such as via wireless communication and/or data transmission); and/or (8) electronically refunding, via one or more processors, the cost of the medical diagnostic exam to the customer or electronically crediting a customer account or providing a discount upon purchase of the insurance product to facilitate providing bound insurance products to online customers. The method may include additional, less, or alternate actions, including those discussed elsewhere herein.

VII. Additional Insurance-Based Embodiments

Figure 6:
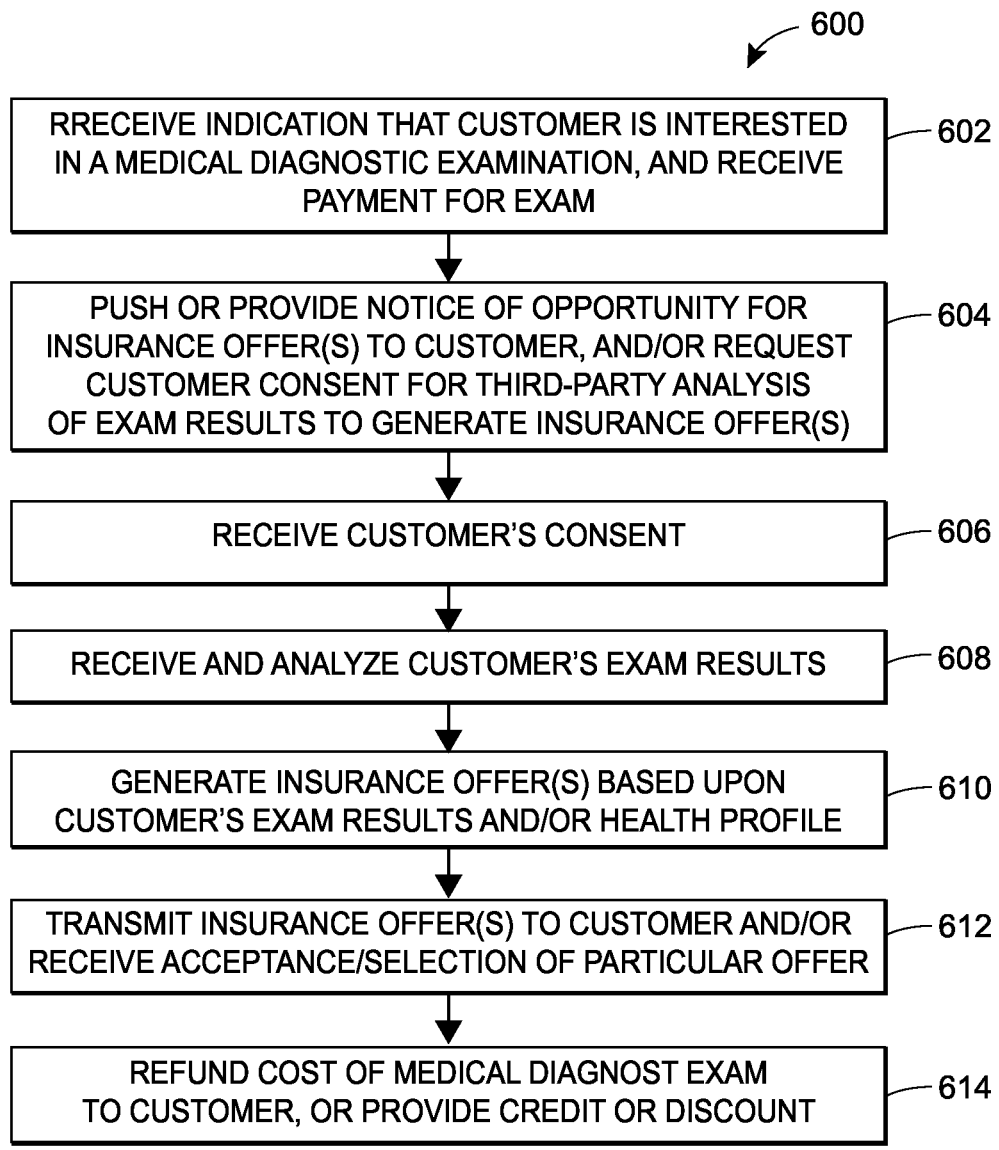

FIG. 6 depicts an exemplary computer-implemented method of providing insurance to a customer 600. The method 600 may be utilized for procuring insurance via an electronic or communications network and based upon customers' medical diagnostic examinations, for example. One or more portions of the method 600 may operate in conjunction with the systems 14, 34, and/or 16-1 to 16N of FIG. 1, the system 300 of FIG. 2, and/or with any one or more portions of the other methods described herein. For example, at least a portion of the method 600 may be executed by one or more processors of the insurance procurement system 14, e.g., by using one or more electronic or communications networks. Additionally or alternatively, at least a portion of the method 600 may be executed by one or more processes of the medical diagnostic provider system 34, e.g., by using one or more electronic communications networks. It is noted that although the method 600 is discussed below with simultaneous reference to FIGS. 1-3, this is merely for ease of discussion, and is not limiting in any way. Generally, the method 600 may be applicable for any number of any types of insurance that require a medical diagnostic examination to be performed on a potential insured party, e.g., life insurance, health insurance, disability insurance, long-term care insurance, etc., but may be equally applicable to other types of insurance, e.g., automobile insurance, personal liability insurance, etc.

In one aspect, the method 600 may include receiving an indication that a customer is interested in having a medical diagnostic exam and receiving payment for the medical diagnostic exam from the customer 604; pushing a notice of the opportunity to receive an insurance offer based upon the medical diagnostic exam results, and requesting customer consent for $3^{rd}$ party (e.g., insurance provider) analysis of the medical diagnostic exam results to generate personalized insurance offer 604; receiving consent from the customer for $3^{rd}$ party analysis of the medical diagnostic exam 606; receiving and analyzing results from the medical diagnostic exam with the customer's consent 608; generating one or more binding quotes for insurance (and/or a health profile) based upon medical diagnostic exam results 610; transmitting the one or more binding quotes for insurance to the customer and/or receiving acceptance and/or selection of a quote or winning bid 612; and/or refunding the cost of the medical diagnostic exam to the customer upon purchase of the insurance product 614. The method may include additional, less, or alternate actions, including those discussed herein, and/or may be implemented via one or more processors or servers (such as processors or servers associated with insurance providers, medical diagnostic providers or laboratories, customers (such as customer mobile devices), insurance lead aggregators, and/or others), and/or computer-executable instructions stored on non-transitory, computer-readable media or medium.

The method 600 may include receiving an indication that a customer is interested in having a medical diagnostic exam and/or receiving payment for the medical diagnostic exam from the customer 604. For instance, customer may schedule a medical diagnostic exam and/or provide online payment for the medical diagnostic exam via the internet and a medical diagnostic provider website, and/or by downloading a client application onto his or her computing device 12, and via which a medical diagnostic examination may be scheduled and payment may be received.

After the medical diagnostic exam has been scheduled, the method 600 may include pushing, sending, or transmitting a notice of the opportunity to receive an insurance offer based upon the medical diagnostic exam results, such as sending the notice to the customer's account associated with the customer's medical diagnostic provider, or directly to their mobile device 604 (e.g., to a web-browser or client application executing on their mobile device 12). Along with the notice, customer consent may be requested for third party (e.g., insurance provider) analysis of the medical diagnostic exam results to generate personalized insurance offers.

The method 600 may include receiving consent from the customer for third party analysis of the medical diagnostic exam 606. For instance, consent from the customer may be transmitted from their mobile device to an insurance provider or medical diagnostic provider remote server or processor via wireless communication and/or data transmission.

The method 600 may include receiving and analyzing results from the medical diagnostic exam with the customer's consent 608. The medical diagnostic exam results may be analyzed for various items, such as those discussed elsewhere herein.

The method 600 may include generating one or more binding quotes for insurance (and/or a health profile) based upon medical diagnostic exam results 610. For instance, a binding quote may be generated from a single insurance provider. Additionally or alternatively, several insurance providers may participate in an online auction, and/or otherwise each insurance provider may provide one or more binding offers for insurance based upon the medical diagnostic exam results.

The method 600 may include transmitting the one or more binding quotes for insurance to the customer and/or receiving acceptance and/or selection of a quote or winning bid 612. For instance, the customer may be able to view several binding quotes via the mobile device, or a $3^{rd}$ party may select winning quote and send the winning quote to the mobile device of the customer for the customer's review and rejection/approval.

The method 600 may include refunding the cost of the medical diagnostic exam to the customer upon purchase of the insurance product 614. For instance, the cost of the medical diagnostic exam may transferred to the customer's bank or credit card account, or may be deducted from the cost of the insurance product.

VIII. Exemplary Computer-Implemented Method

Figure 7:
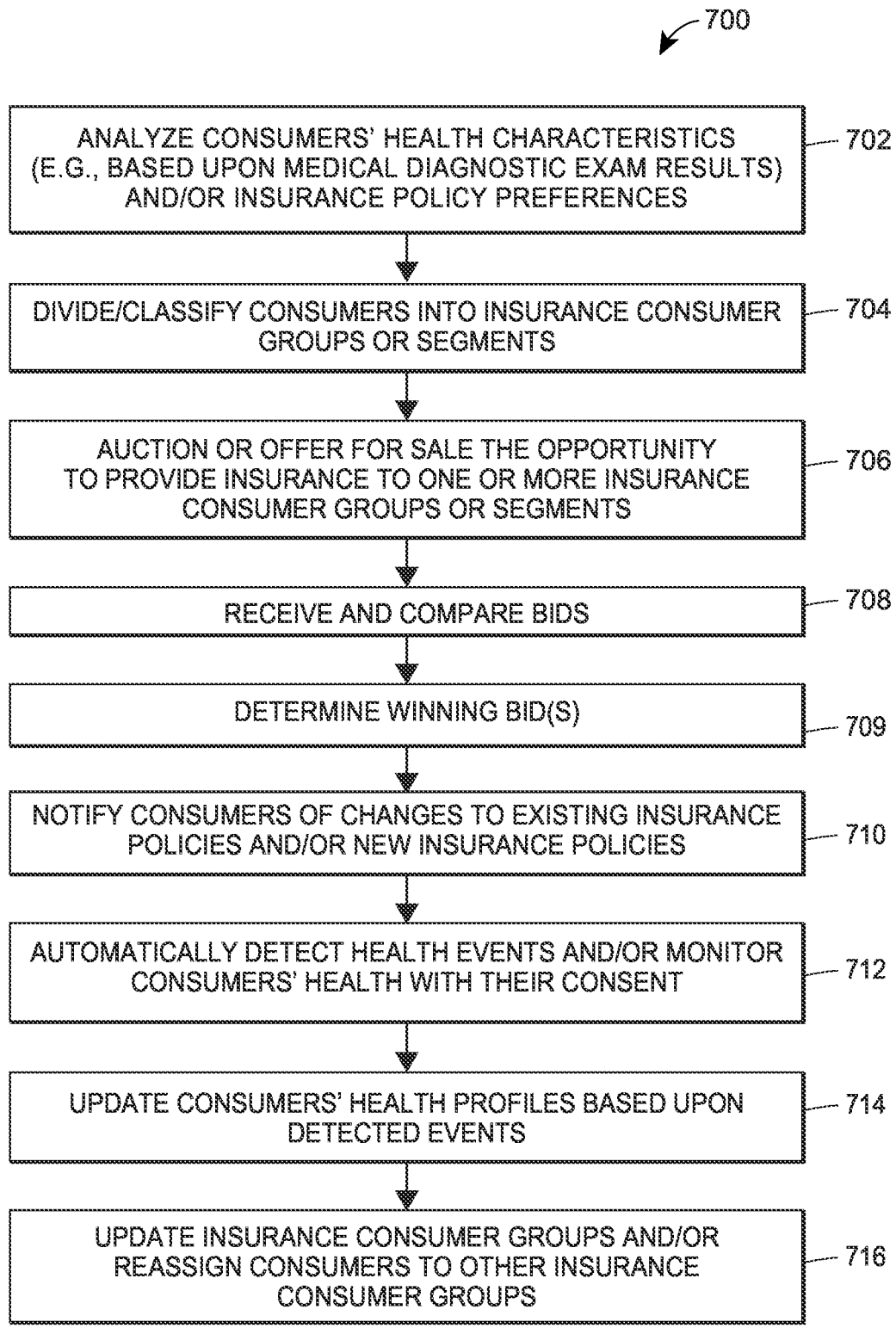
FIG. 7 depicts an exemplary computer-implemented method of auctioning groups or bundles of life or other health-related insurance policies.

FIG. 7 illustrates an exemplary computer-implemented method 700. The method 700 may be utilized for procuring insurance via an electronic or communications network and based upon consumers' or customers' medical diagnostic examinations, for example. One or more portions of the method 700 may operate in conjunction with the systems 14, 34, and/or 16-1 to 16N of FIG. 1, the system 300 of FIG. 2, and/or with any one or more portions of the other methods described herein. For example, at least a portion of the method 700 may be executed by one or more processors of the insurance procurement system 14, e.g., by using one or more electronic or communications networks. Additionally or alternatively, at least a portion of the method 700 may be executed by one or more processes of the medical diagnostic provider system 34, e.g., by using one or more electronic communications networks.

It is noted that although the method 700 is discussed below with simultaneous reference to FIGS. 1-3, this is merely for ease of discussion, and is not limiting in any way. Generally, the method 700 may be applicable for any number of any types of insurance that require a medical diagnostic examination to be performed on a potential insured party, e.g., life insurance, health insurance, disability insurance, long-term care insurance, etc., but may be equally applicable to other types of insurance, e.g., automobile insurance, personal liability insurance, etc.

The method 700 may include, via one or more processors, computing devices, or servers: with customers' permission or consent, analyzing insurance customers (e.g., existing or potential insurance customers) by health characteristics and/or insurance policy preferences 702; dividing and/or classifying insurance customers into groups or segments based upon the health characteristics and/or insurance preferences 704; auctioning or offering for sale the opportunity to provide medical diagnostic-related insurance to one or more of the customer groups or segments 706; receiving and comparing one or more bids 708; accepting one or more winning bids 709; notifying insurance customers of new insurance policies and/or of changes to existing insurance policies, premiums, discounts, etc. 710; automatically detecting events that may impact a risk associated with, or the health of, a customer, or otherwise monitoring a customer's health with their consent 712; updating the customer's health profile or risk score based upon the detected event 714; and/or updating the customer' insurance group and/or moving the customer to a new insurance group 716. After a number of customers have been moved to new or different risk insurance groups, another auction of the new or updated groups may be held 706, the process may continue 708, 710, 712, 714, 716, etc. The method may include additional, fewer, or alternate actions, including those discussed elsewhere herein.

In particular, the method 700 may include, via one or more processors, computing devices, or servers, analyzing insurance customers by their health characteristics and/or insurance policy preferences 702. The analysis of customers may be by insurance policy preferences, such as by insurance coverages, deductibles, and/or limits typically desired or requested by an individual customer. For instance, a group of insurance customers may prefer to have: $500,000 (or other amounts) of coverage for various life or health insurance policies; certain types of coverages and/or insurance; certain levels of deductibles; premiums under $500 per month; etc. Thus, groups of similarly minded customers may be grouped together based upon similar coverages, deductibles, and/or limits that they may typically prefer for various types of insurance. Additionally or alternatively, groups of similarly minded customers may be grouped together based upon similar customer health characteristics.

In one embodiment, customer health characteristics may be analyzed 702 after customers have given their affirmative consent or permission to release medical information, and subsequently the customers' medical diagnostic examination results (or portions thereof) may be analyzed to determine respective health characteristics. Characteristics that may be analyzed by the one or more processors may include customer risk, risk scores, age, status (such as married or single), occupation, geographical location, life style, drinking or smoking habits, body mass index, blood pressure level, chronic conditions, medications, etc.

One or more processors may access a database, customer examination results, and/or customer health profiles that are stored in one or more memory units to analyze the customer health characteristics and/or customer insurance policy preferences. For example, a database storing customer health characteristics and/or customer insurance policy preferences may be accessible to the insurance procurement system 14, and/or to the insurance provider systems 16-1 to 16-N. In some embodiments, each insurance provider systems 16-1 to 16-N may only access its own respective customer database.

In one embodiment, analyzing insurance customers by health characteristics 702 may include analyzing health profiles of insurance customers which have been determined based upon results of respective medical diagnostic examinations that have been performed on the customers. For example, a health profiler unit 20 may generate health profiles of customers based upon stored exam results in the database 30, and the generated health profiles may be analyzed (block 702).

The method 700 may include, via the one or more processors, computing devices or servers, dividing and/or classifying insurance customers into groups or segments 704, e.g., based upon the results of the analysis 702. Based upon the analysis of customers mentioned above, such as computer analysis of customer health or life style characteristics and/or customer health-related insurance policy preferences, the customers may be divided into groups or segments of customers having similar characteristics or preferences. For example, multiple groups or segments of a set of customers may be determined based upon contents of health profiles of the set of customers, e.g., common range of particular health characteristics, omission of certain health conditions, etc. Various groups and/or segments of the set of customers may be determined additionally or alternatively based upon other criteria. For instance, one group or segment of insurance customers may be characterized as (1) low risk or having a risk score within a given range; (2) carrying out certain life styles (such as life styles involving little or no smoking or drinking, little travel; little dangerous activities (lack of sky diving, downhill skiing, scuba diving, etc.); (3) living within a given state, city, or zip code; (4) having one or more deductible preferences; (5) having one or more coverage preferences; (6) having one or more common characteristics (age, chronic conditions, occupation, etc.); and/or (7) other common factors.

In one embodiment, insurance customer groups, groupings, or segments may be additionally or alternatively defined by behavioral and attitudinal segmentation and/or customer criteria, such as occupation, risk characteristics, insurance claims expectations, insurance company ratings, driving behavior (e.g., as determined by telematics data), etc. Other customer groups may be defined, including those discussed elsewhere herein.

The method 700 may include, via the one or more processors, computing devices or servers, and via one or more electronic or communications networks, auctioning or offering for sale the opportunity to provide health-related insurance (e.g., life, burial, accidental death, health, etc.) to one or more of the customer groups or segments 706. In one embodiment, each group of insurance customers having common health characteristics and/or insurance policy preferences may be presented to potential bidders (e.g., insurance provider systems 16-1 to 16-N) via an electronic or online auction for the opportunity to provide insurance for the group of customers. For instance, the one or more processors, computing devices or servers may cause one or more insurance customer groups to be presented and/or offered for sale on remote display screens (such as via the Internet or a secure communications network), e.g., in conjunction with respective indications of their common or similar health characteristics and/or insurance preferences.

The method 700 may include, via the one or more processors, computing devices or servers, receiving one or more bids 708, e.g., from at least some of the insurance provider systems 16-1 to 16-N, and/or via one or more electronic or communications networks. Bidders for the various groups of similarly situated and/or like-minded insurance customers (such as grouped by low or medium risk life styles, insureds with the same preferences for deductibles or coverages, insureds having similar driving behaviors (as evidenced by telematics data), etc.) may submit their bids via remote computers, e.g., computers of the systems 16-1 to 16-N. The bids may be received by a processor or server associated with the entity running the auction via wireless or wired communication and/or data transmission, e.g., one or more processors of the insurance procurement system 14 or of the medical diagnostic provider system 34.

The method 700 may include, via the one or more processors, computing devices or servers, determining a winning bid from the set of received bids 709. Determining the winning bid 709 may include, for example, comparing the one or more bids against a set of pre-determined, prioritized criteria, such as premium cost, insurance provider rating, compatibility of the bid with the range of preferences specified by the group's customers, etc. In some embodiments, determining the winning bid 709 may include accepting the winning bid and notifying the corresponding insurance provider system 16. If the winning bid includes a binding quote, insurance may thereby be automatically obtained or procured for (e.g., on behalf of) the customers included in the group, e.g., in a manner similar to as previously described above.

The method 700 may include, via the one or more processors, computing devices or servers, notifying insurance customers of new life or health-related insurance policies, premiums, discounts, etc. 710, e.g. by using one or more electronic and/or communications networks. After a winning bid has been determined or selected, new life or health-related insurance policies, rates, premiums, discounts, etc. may be determined or updated. New insurance policies and associated information may be communicated to the insureds that may be impacted by the auction, such as notified of reduced premiums and/or increased discounts (such as increased discounts for low risk driving behavior). The determination or selection of a winning bid may be performed by the customer (e.g. via his or her computing device 12), and/or by the medical diagnostic system 34 or the insurance procurement system 14, e.g., when the customer had given his or her previous consent for the system 34 or 14 to procure insurance on the customer's behalf. In some embodiments, a winning bid may result in a change to a customer's existing health-related policy. For example, a premium amount may be decreased, a coverage maximum may be increased, etc. In these situations, the customer may be notified of the changes to his or her existing insurance coverage (block 710).

The method 700 may include, via the one or more processors, computing devices or servers, automatically detecting health-related events or other events that may impact a risk associated with a customer or customers 712. Over time, risk associated with each customer may change. One customer may engage in low risk behavior, and/or not be involved with automobile accidents, and/or not report any insurance claims or any health issues. On the hand, other customer may be involved in a high number of automobile accidents and/or otherwise engage in risky driving behavior, or engage in high-risk activities (skiing, scuba diving, surfing, etc.). As a result, risk associated with various customers (or risk scores) may be lowered or increased over time based upon data analysis by one or more processors, such as by a processor associated with an insurance provider and/or medical diagnostic provider, and with the permission of the insured. For instance, insureds engaging in low-risk behavior may desire for their information to be analyzed by an insurance provider to achieve a discount on various insurance products. The data may by gathered by one or more processors, such as from a customer profile and/or from third party sources, such as a DMV (Department of Motor Vehicles) or social media websites. Additionally or alternatively, the data may be telematics data that is gathered by a mobile device (e.g., smart phone) and/or a conventional telematics device that plugs into an electrical or computer system of a vehicle.

Additionally or alternatively, changes to customers' health profiles may also change over time, and may impact customers' risk scores. Changes to customers' health profiles may be determined or detected (block 712), for example, by receiving an indication of updates and/or changes to the customer's health from the medical diagnostic provider system 34, and/or by receiving input from the customer 12.

The method 700 may include, via the one or more processors, computing devices or servers, updating the customer's or customers' health profile or risk score 714. Based upon the data gathered and/or collected by one or more processors, each customer's health profile, risk profile, and/or risk score may be updated to reflect low or high-risk behavior. For instance, a customer's profile may reflect more recent customer preferences for various insurance policy coverages, deductibles, limits, etc. The customer profile may also be updated to reflect more recent customer preferences for various types of insurance or insurance products that the customer may be interested in, such as life, health, burial, auto, homeowners, or other insurance. As another example, a customer's risk score or profile for automobile insurance may be updated based upon a lack of accidents for a given period of time, and/or involvement in one or more vehicle accidents. The cause of the vehicle accidents may also be factored into the risk score or profile.

The method 700 may include, via the one or more processors, updating the customer group or segment to which a customer belongs or is assigned, and/or moving or reassigning the customer to a new group 716. For instance, based upon a customer's updated health profile and/or risk score, an individual customer may be moved, via one or more processors, to be associated with a new or different customer group or segment. Additionally or alternatively, based upon a customer's more recent preferences for insurance policy coverages, deductibles, or limits, and/or types of insurance products, an individual customer may be moved, by the one or more processors, to be associated with a new or different customer group or segment.

The method 700 may include, via the one or more processors, computing devices or servers, after a number of customers have been moved to new or different risk-based groups, having or holding another auction of the new or updated groups 706, and then the process 700 may continue (as shown in FIG. 7). For instance, after a number of customers have been moved to a new or different group of insurance customers based upon their personal characteristics (education, marital status, age, driving record or history, etc.) and/or insurance policy preferences (new interest in life or health insurance, new interest in home owners insurance, changed policy deductibles or coverages, interest in using telematics devices and/or gathering telematics data, etc.), a new electronic or online auction of the new, or revised/updated group of insurance policies associated with those insurance customers for which personal characteristics and/or insurance policies have changed may be held, such as under the direction of one or more processors.

It is noted that while the method 700 above is described with respect to a group of insurance customers, most of the techniques therein may be easily applied to an individual insurance customer. For example, the health profile of an individual customer may be auctioned or offered for sale (block 706), resulting bids may be compared (block 708), a winning bid may be selected (block 709), and the individual customer may be notified of a change to an existing policy or a possible new insurance policy (block 710). Similarly, changes to the health condition, other characteristics, and/or other preferences of the individual customer may be detected or determined (block 712), and the risk score and/or health profile of the individual customer may be updated based upon the changes (block 714). Based upon the updated risk score and/or health profile of individual customer, his or her existing insurance policy may be updated or a new policy may be established (block 716), e.g. by utilizing an auctioning technique (blocks 706, 708, 709).

Figure 8:
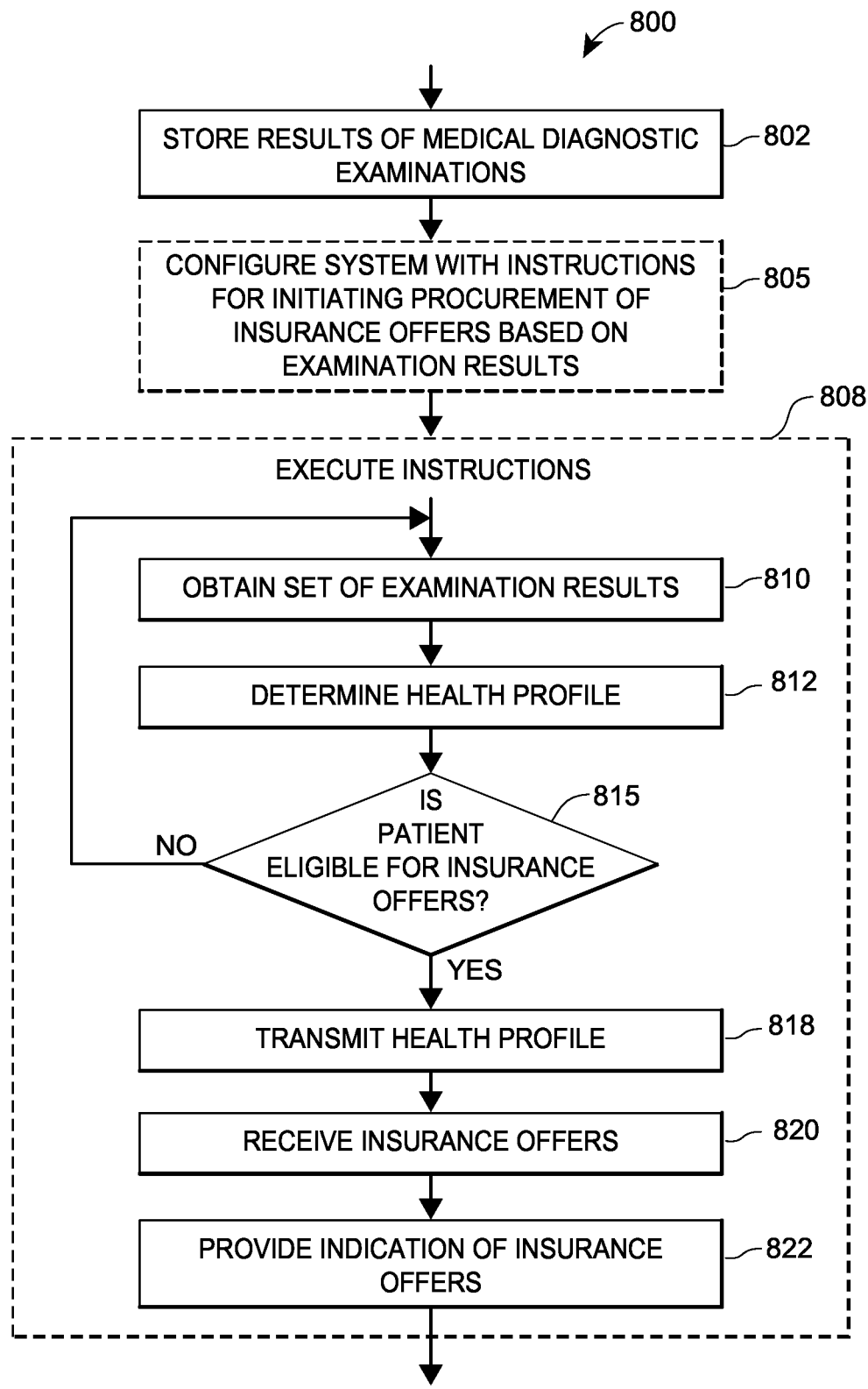
FIG. 8 depicts an exemplary method for providing or initiating offers for insurance based upon medical diagnostic examinations.

IX. Exemplary Method for Initiating Procurement of Insurance Based Upon Medical Diagnostic Examinations FIG. 8 illustrates an exemplary computer-implemented method 800 of providing insurance based upon medical diagnostic examinations, e.g., via an electronic or communications network. That is, FIG. 8 illustrates an exemplary computer-implemented method for initiating offers for insurance based upon medical diagnostic examinations. In one embodiment, at least a portion of the method 800 may be performed using the insurance procurement system 14 of FIG. 1 and/or by the computer system 300 of FIG. 2. For example, at least a portion of the method 800 may be performed by one or more of the health profiler unit 20, the eligibility determiner unit 21, the provider selector unit 22, the policy procurement unit 24, and/or the notification unit 26. Indeed, one or more portions of the method 800 may operate in conjunction with the systems 14, 34, and/or 16-1 to 16N of FIG. 1, the system 300 of FIG. 2, and/or with any one or more portions of the other methods described herein.

It is noted that although the method 800 is discussed below with simultaneous reference to FIGS. 1-3, this is merely for ease of discussion, and is not limiting in any way. Generally, the method 800 may be applicable for any number of any types of insurance that require a medical diagnostic examination to be performed on a potential insured party, e.g., life insurance, health insurance, disability insurance, long-term care insurance, etc., but may be equally applicable to other types of insurance, e.g., automobile insurance, personal liability insurance, etc.

It is noted that although the method 800 is discussed below with simultaneous reference to FIGS. 1-3, this is merely for ease of discussion, and is not limiting in any way. Generally, the method 800 may be applicable for any number of any types of insurance that require a medical diagnostic examination to be performed on a potential insured party, e.g., life insurance, health insurance, disability insurance, long-term care insurance, etc., but may be equally applicable to other types of insurance, e.g., automobile insurance, personal liability insurance, etc.

The method 800 may include, in one embodiment, storing respective sets of results (or portions thereof) of medical diagnostic examinations that have been performed on one or more patients or subjects by one or more medical diagnostic providers (block 802). For example, the examination results may be stored at the medical diagnostic provider system 34 and/or at the insurance procurement system 14, e.g., in the examination results database 30. The method 800 may also include particularly configuring one or more tangible, non-transitory memories of the system storing thereon particular computer-executable instructions for initiating the procurement of insurance offers based upon medical diagnostic examinations and/or based upon their results (block 805);

and/or executing, by one or more processors of the system, the particular computer-executable instructions (block 808).

The execution of the particular computer-executable instructions 808 may cause the system, with the customer's permission, to obtain a set of stored medical diagnostic examination results of a patient, customer, or consumer (block 810), where the results were generated from a medical diagnostic examination that was performed on the patient; determine or generate a health profile of the patient on which the examination was performed (block 812); and/or determine, based upon the contents of the health profile of the patient, whether or not the patient is eligible for one or more offers for one or more types of insurance that require medical diagnostic examinations to be performed on applicants or on potential insured parties (block 815). At the block 815, when or if the patient or subject is determined as being ineligible for one or more offers of insurance, the method 800 returns to the block 810, e.g., so that another patient's medical diagnostic examination results may be analyzed. However, at the block 815, when or if the patient is determined as being eligible for one or more offers for insurance, the method 800 may include providing or transmitting the patient's health profile to one or more insurance provider computing systems (block 818); receiving, in response to the transmission of health profile, one or more insurance offers comprising one or more binding quotes for one or more insurance policies for which the patient has been determined to be an eligible or approved insured party (block 820); and/or providing an indication of the one or more binding quotes to a user, thereby providing the one or more offers for the one or more types of insurance (block 822).

The method may include additional, fewer, or alternate actions, including those discussed elsewhere herein. For example, in some embodiments, the blocks 805 and 808 are at least partially omitted, for example, when one or more of the blocks 810-822 are performed by hardware, firmware, and/or any other suitable means for implementing the health profiler unit 20, the eligibility determiner unit 21, the provider selector unit 22, the policy procurement unit 24, and/or the notification unit 26.

Specifically, at the block 802, the method 800 may include storing one or more sets of results of medical diagnostic examinations that have been performed on respective patients or respective subjects by one or more medical diagnostic providers. As previously discussed, typically, the medical diagnostic examinations may have been performed on patients by one or more medical diagnostic providers, physicians or other medical professionals, medical diagnostic laboratories, and/or the like. Typically, each of the medical diagnostic examinations may have included at least one invasive procedure, such as a blood draw and analysis, and in some scenarios, the medical examination may have performed as part of the patient's annual physical examination. The sets of medical examination results may be stored at the medical diagnostic provider computing system 34, for example. Additionally or alternatively, at least some of the sets of examination results (or copies thereof) may be stored (block 802) in the examination database 30 of FIG. 1, and the data or information stored therein may be accessible or otherwise made available to the insurance procurement system 14.

The method 800 may also include particularly configuring one or more tangible, non-transitory memories of the system by storing thereon particular computer-executable instructions for initiating procurement of insurance offers based upon medical diagnostic examinations and/or their results (block 805). Referring to FIG. 2 as an illustrative but non-limiting example, the particular computer-executable instructions may be included in the application programs 335 stored on the RAM 332 and/or in the application programs 345 stored on the hard disk drive 341, thereby particularly configuring the computing system 300. The particular computer-executable instructions may have been downloaded or otherwise transferred to the computing system 300, such as via a network interface 370, the persistent memory port 351, or the optical disk port 355, for example.

Further, the method 800 may include executing, by one or more processors of the system, the particular computer-executable instructions stored in the therein (block 808). In one embodiment, the execution of the particular computer-executable instructions 808 may cause the system to automatically initiate the procurement of insurance offers based upon medical diagnostic examination results. For example, the execution of the particular computer-executable instructions 808 may cause one or more of blocks 810-822 to be executed. As previously discussed, though, in some embodiments of the method 800, at least part of the blocks 805 and/or 808 are omitted, and in some embodiments, the method 800 includes additional blocks that are not shown.

At any rate, the method 800 may include obtaining one or more stored sets of examination results (block 810) by using any suitable manner or technique. For example, the initial storing or writing of examination results into medical records data storage (block 802) may cause the system 14 to be notified of the newly added records, thus prompting the system 14 to access the newly added records. In another example, the system 14 may obtain a shadow copy of at least some of the records that are stored in a master medical records database, e.g., by automatic receipt or explicit request. In still another example, the system 14 may periodically and/or on-demand request or access the master medical records database for newly stored results, etc.

At a block 812, the method 800 may include determining or generating, for a particular obtained set of medical diagnostic examination results, a corresponding health profile of the respective patient, consumer, customer, or subject on which the examination was performed. As previously discussed, the contents of a health profile typically includes a subset of data extracted or generated based upon the data and/or information stored in the respective set of medical diagnostic examination results. For example, data included in the respective set of medical diagnostic examination results may be aggregated, average, and/or otherwise combined to generate the patient's health profile. The patient's health profile may be generated by a medical diagnostic provider system 34 or by an insurance procurement system 14 based upon the patient's stored examination results, for example.

Additionally, the method 800 may include determining, based upon the health profile of the respective patient or subject, whether or not the patient or subject is eligible for one or more offers for one or more types of insurance that require medical diagnostic examinations to be performed on applicants or potential insured parties, such as health insurance, life insurance, disability insurance, etc. (block 815). In one embodiment, the determination may be made additionally based upon information, data, boundary conditions, and/or other criteria provided by each of the insurance providers 16-1 to 16-N, indications of which may be stored in the provider database 32. Additionally or alternatively, the determination may be made based upon information, data, boundary conditions, and/or other criteria that are provided by the medical diagnostic provider and/or by the insurance procurer. If or when the patient is determined to be ineligible for one or more offers of insurance, the method 800 may return to the block 810 to obtain another set of examination results of another patient. In some embodiments, the block 815 may be omitted, e.g., when the patient is assumed to be automatically eligible.

At the block 815, if or when the patient is determined to be eligible for one or more offers of one or more types of insurance, the method 800 may include providing or transmitting the health profile of the patient to one or more recipient insurance provider computing systems to which the system is communicatively coupled (block 818), e.g., via one or more network interfaces that communicatively couple the system to the recipient insurance provider computing systems for bid or the generation of one or more insurance offers for which the patient may be an insured party.

In one embodiment, providing or transmitting the health profile of the patient is based upon an assent or consent of the patient (or his or her agent), e.g., to release the examination results and/or other medical information to one or more third parties. For example, the method 800 may include obtaining the assent, consent, or permission to release medical information of the patient, and the block 818 is executed only when the permission to release the patient's medical information has been granted. The assent of the patient or the patient's agent may be obtained in conjunction with the patient's medical diagnostic examination or the patient's assent may be obtained at any other time prior to the execution of the block 818 (e.g., via a user interface and/or one or more network interfaces). In one embodiment, an indication of the patient's assent, consent, or granted permission to release medical information may be stored in the one or more data storage devices of the medical diagnostic provider computing system 34 and/or in conjunction with the patient's medical diagnostic examination results (e.g., in the exam results database 30).

In one embodiment (not shown), the method 800 may include obtaining an indication of one or more preferred insurance policy terms, such as a desired or preferred amount of a premium payment, term length, insurance provider rating, type of insurance, payout amount, annuity amount, settlement option, and/or other insurance policy term. One or more of the preferred insurance terms may be indicated by the patient, the patient's agent, and/or by the insurance procurement system (e.g., the system 14 or the system 300), such as in conjunction with the patient's medical examination, in conjunction with the patient's consent to release medical information, or at any other time prior to the execution of the block 818. For example, the patient or the patient's agent may queried (asynchronously with the execution of his or medical examination) as to if he or she has any preferences for insurance terms (e.g., via a user interface and/or one or more network interfaces), and the preferences of the patient may be stored with his or her medical examination results. When one or more preferred insurance policy terms are obtained or otherwise available, at least one of the available preferred insurance policy terms may be transmitted in conjunction with the patient's health profile (block 818) for use by the insurance provider computing systems to utilize in generating their respective insurance offers.

In some embodiments (not illustrated), prior to transmitting the health profile of the patient to one or more recipient insurance provider computing systems (block 818), the method 800 may include determining or selecting the particular recipient insurance provider computing systems. Referring to FIG. 1 as an illustrative but non-limiting example, the system 14 may determine or select which of the insurance provider computing systems 16-1 through 16-N is or are to receive the patient's health profile, e.g., for bidding purposes. The determination or selection of recipient insurance provider computing systems may be based upon the aforementioned one or more preferred insurance policy terms, for example, one or more insurance preferences and/or requirements indicated by the patient, his or her agent, and/or insurance procurer; one or more characteristics of the insurance providers 16-1 to 16-N (e.g., as indicated by the provider database 32, such as the types of insurance that are respectively provided by each of the providers 16-1 through 16-N); an availability of each of the insurance provider computing systems 16-1 through 16-N; and/or based upon other criteria.

Each recipient insurance provider computing system may determine, based upon the contents of the received health profile (and optionally on any received preferred insurance policy terms), whether or not the patient or subject is an eligible and/or approved insured party for one or more offers for insurance that are able to be provided by recipient insurance provider. Consequently, one or more recipient insurance provider computing systems may determine, generate, and return, to the system, one or more insurance offers comprising one or more offers for insurance for which the patient is an approved insured party. In one embodiment, the one or more offers for insurance are not merely estimates or non-binding quotes for insurance; instead, the one or more offers for insurance comprise binding quotes, where the acceptance of one of the binding quotes results in a legal contract for insurance.

Moreover, the initial generation of one or more insurance offers for the patient at respective insurance provider computing systems may have been initially triggered or initiated at the respective insurance provider computing systems only based upon the reception of the patient's health profile (and optionally of indicated insurance preferences and/or requirements) at the respective insurance provider computing systems so that the one or more insurance offers are an initial set of insurance offers that are generated for the patient. For example, a specific responding insurance provider computing system may not initiate or begin generating an insurance offer for the patient until the patient's health profile is received at the specific responding insurance provider computing system from the system (e.g., from the insurance procurement system 14 or from the computing system 300). That is, the respective insurance provider computing system does not receive (from the system 14, the system 300, any other system, or any user interface) any partial personal information corresponding to the and relating to the generation of the one or more insurance offers prior to receiving the patient's health profile from the system (e.g., from the system 14 or the system 300). Indeed, in some cases, the patient's health profile is the sole or only indication of a quality of health of the patient that is received by the respective insurance provider computing system, and the one or more insurance offers may be generated from the sole indication of the patient's quality of health.

Thus, as one or more offers for insurance may be provided to the system by one or more recipient insurance provider computing systems, the method 800 may further include receiving one or more offers for insurance corresponding to one or more respective insurance policies for which the patient or subject is eligible as an insured party (block 820). Additionally, the method 800 may still further include providing an indication of the one or more offers for insurance to a user (block 822), e.g., via a user interface, via one or more networks, by email, by physical letter, and/or electronically at a user interface of the user computing device 12, the medical diagnostic provider system 34, the insurance procurement system 14, and/or any one of the insurance provider systems 16-1 to 16-N, etc., thereby initiating the one or more offers for insurance based upon the patient's medical diagnostic examination results.

The method 800 may include determining that one of the one or more offers for insurance provided at the block 822 has been selected, e.g., by the patient, the patient's agent, another user, by the procurement system (e.g., the system 14 or the system 300), and/or another computing system (not shown). For example, the method 800 may include receiving an indication of the selected offer for insurance from the customer 12. In another example, the method 800 may include the system 14 selecting a particular offer for insurance based upon one or more selection criteria which may be indicated, for example, by the obtained one or more preferred insurance policy terms. The selection criteria may include an indication of an order of priority and/or importance of various criteria, and the method 800 may include comparing the received plurality of insurance offers against the criteria and optionally, their relative priority (not shown). For example, the system may compare the received plurality of insurance offers based upon one or more insurance preferences and/or requirements indicated by the patient or consumer, and optionally based upon a prioritization of the preferences and/or requirements that have been previously indicated. If no insurance preferences and/or requirements have been otherwise indicated, the system may compare the received plurality of insurance offers based upon one or more default criteria, e.g., the lowest monthly premium amount.

The method 800 may include accepting the selected binding quote on behalf of the patient or the patient's agent (not shown). For example, permission to accept a binding quote on behalf of the patient based upon the results of the patient's medical diagnostic examination results may have been granted in conjunction with his or her medical diagnostic examination. In one embodiment, determining the selection of binding quote includes accepting the selected binding quote on behalf of the patient, thereby resulting in a legal contract for insurance.

The method 800 may further include providing an indication of the selected binding quote to the insurance provider computing system 16x that provided or generated the selected binding quote in response to receiving the patient's health profile (not shown). The insurance provider computing system 16x, upon being notified that its insurance offer has been selected, may proceed to underwrite, bind, and/or perform other actions to move the insurance policy to being in an "in-force" state. Further, the insurance provider computing system 16x may provide indications notifications that one or more of the actions has been completed, e.g., that the policy has been underwritten, that the policy has been bound, that the policy is in force, etc. As such, the method 800 may include receiving, e.g. at the system, one or more indications of these and/or other actions that have been completed by the insurance provider computing system 16x to move the insurance policy towards being in-force.

In some embodiments (not shown), the method 800 may include initiating at least a partial refund of the cost of the medical diagnostic examination. Additionally or alternatively, the method 800 may include initiating a credit corresponding to at least a portion of the cost of the medical diagnostic examination towards future premiums and/or fees of the insurance policy. For example, upon receiving notification that the insurance policy has been bound, the method 800 may initiate at least one of the refund or the credit.

In some embodiments, at least some of the blocks 810-822 are included in an automated auction of the patient's health profile, such as described in aforementioned U.S. Patent Application No. 62/104,596, or some other suitable automated auction. Auctioning the patient's health profile may further include selecting one of the received plurality of insurance offers. For example, the system may receive an indication of preferences, requirements, and/or priorities of one or more insurance characteristics, and the system may automatically select the one of the returned insurance offers that best meets the indicated preferences, requirements and/or priorities (or alternatively, that best meets the one or more default criteria). The system may automatically provide the selected insurance offer to the patient, patient's agent, and/or another user.

While the method 800 has been described above with respect to a particular patient, this is only one of many embodiments. For example, a particular patient's health profile may be grouped with the health profiles of other patients, and the group of health profiles may be auctioned to various insurance providers and at least some of the insurance providers may return one or more bids for the group of health profiles, e.g., in a manner such as described in aforementioned U.S. Patent Application No. 62/104,596. Indeed, any one or more of the techniques described herein for initiating the procurement of insurance based upon medical diagnostic examinations may operate in conjunction with one or more aspects of U.S. Patent Application No. 62/104,596, if desired. In some embodiments, though, patient health profiles are not auctioned, and are merely sent out to one or more insurance provider systems for a single round of bidding.

Further, the method 800 may be utilized for one or more sets of medical diagnostic examination records, and/or with one or more different insurance providers. In an example scenario, the method 800 may obtain a single set of examination results for a particular patient (block 810), and may transmit the health profile of said patient to multiple different insurance providers' systems (block 818) e.g., to automatically initiate offers for insurance based upon the patient's medical diagnostic examination results. In another example scenario, the method 800 may obtain multiple sets of medical diagnostic examination results corresponding to multiple patients (block 810), and respective health profiles for each of the sets of results may be transmitted to a single insurance provider's system (818), e.g., to automatically initiate offers for insurance based upon the patients' medical diagnostic examination results.

Still further, in the method 800, the offers that are received from the one or more insurance providers system's (block 820) may be binding offers or quotes for insurance, or may be non-binding offers or quotes for insurance. Additionally, as previously discussed, in some embodiments, the method 800 may automatically select one of the received offers, while in some embodiments of the method 800, the patient or the patient's agent may select one of the received offers. Also as previously discussed, in some embodiments, the method 800 may automatically cause the selected offer to be bound, thereby automatically providing insurance for the patient based upon his or her medical diagnostic examination results.

X. Additional Considerations

The following additional considerations apply to the foregoing discussion. Throughout this specification, plural instances may implement operations or structures described as a single instance. Although individual operations of one or more methods are illustrated and described as separate operations, one or more of the individual operations may be performed concurrently, and nothing requires that the operations be performed in the order illustrated. These and other variations, modifications, additions, and improvements fall within the scope of the subject matter herein.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of "a" or "an" is employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a system and a process of automatically obtaining and/or maintaining insurance coverage through the principles disclosed herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein without departing from the spirit and scope defined in the appended claims.

The patent claims at the end of this patent application are not intended to be construed under 35 U.S.C. § 112(f) unless traditional means-plus-function language is expressly recited, such as "means for" or "step for" language being explicitly recited in the claim(s).

The invention claimed is:
1. A system comprising:
one or more processors;
a network interface configured to communicatively couple the system to a plurality of insurance provider computing systems for respective ones of a plurality of insurance providers; and
one or more tangible, non-transitory memories storing computer-executable instructions that, when executed by the one or more processors, cause the system to:
prior to requesting partial personal health information and prior to receiving a non-binding offer, schedule or set up an appointment for a person with a medical diagnostic provider for a medical diagnostic examination;
generate a health profile for the person based upon the results of the medical diagnostic examination completed for the person;
transmit, via the network interface, the health profile for the person to the plurality of insurance provider computing systems;
trigger generation, based upon the health profile, of a plurality of underwritten binding quotes for a plurality of insurance policy offers that the person is eligible for as a pre-approved potential insured party from the plurality of insurance providers by providing, using the network interface, the health profile for the person to the plurality of insurance provider computing systems associated with the plurality of insurance policy offers;
present, at a user interface, the plurality of underwritten binding quotes that are generated based upon the completion of the medical diagnostic examination for the person; and
receive, at the user interface, a selection of one of the plurality of underwritten binding quotes.

2. The system of claim 1, wherein the system is operated and/or provided by a medical diagnostic provider that completed the medical diagnostic examination for the person.

3. The system of claim 1, wherein the system is operated and/or provided by an insurance provider and/or by an insurance procurer, the network interface communicatively connects the system to a computing system operated and/or provided by the medical diagnostic provider, and wherein the results of the person's medical diagnostic examination are stored at the medical diagnostic provider computing system.

4. The system of claim 1, wherein the plurality of insurance policy offers includes offers for at least one of a life insurance policy, a long-term care insurance policy, or a disability insurance policy.

5. The system of claim 1, wherein the plurality of insurance policy offers includes different types of insurance policies.

6. The system of claim 1, wherein the computer-executable instructions, when executed by the one or more processors, cause the system to:
provide, via the network interface, an indication that the one of the binding quotes has been selected to the respective insurance provider computing system.

7. The system of claim 6, wherein the computer-executable instructions, when executed by the one or more processors, cause the system to:
receive an indication that the one of the plurality of underwritten binding quotes has been bound by the respective insurance provider; and
at least one of refund or credit to the person a cost of the medical diagnostic examination completed for the person upon receiving the indication that the one of the plurality of underwritten binding quotes has been bound.

8. The system of claim 1,
wherein the plurality of underwritten binding quotes are determined based upon the health profile of the person and one or more preferred insurance policy terms from a group of terms comprising an amount of a premium payment, a term length, an insurance provider rating, a desired type of insurance, a payout amount, an annuity amount, a settlement option, and another insurance policy term, and
wherein at least some of the members of the group of terms are defined by at least one of the person, an agent of the person, or the insurance provider.

9. The system of claim 1, wherein the medical diagnostic examination completed for the person includes at least one of (i) an invasive procedure, or (ii) is performed as part of an annual physical examination of the person.

10. The system of claim 1, wherein the generation of the plurality of underwritten binding quotes comprises an auction of the health profile of the person to the plurality of insurance provider computing systems.

11. A computer-implemented method for initiating offers for insurance based upon a medical diagnostic examination performed by a medical diagnostic provider on a person, the method comprising:
prior to requesting partial personal health information and prior to receiving a non-binding offer, scheduling or setting up, via one or more processors, an appointment for the person with the medical diagnostic provider for the medical diagnostic examination;
generating, by the one or more processors, a health profile for the person based upon the medical diagnostic examination performed by the medical diagnostic provider on the person;
transmitting, by the one or more processors, the health profile for the person to a plurality of insurance provider computing systems that are operated and/or provided by a plurality of insurance providers;
triggering generation, by the one or more processors and based upon the health profile for the person, of a plurality of underwritten binding quotes for a plurality of insurance policy offers that the person is eligible for as a pre-approved potential insured party from the plurality of insurance providers by providing the health profile for the person to the plurality of insurance provider computing systems associated with the plurality of insurance policy offers;
presenting, at a user interface, the plurality of underwritten binding quotes that are generated based upon completion of the medical diagnostic examination on the person; and
receiving, at the user interface, a selection of one of the plurality of underwritten binding quotes.

12. The computer-implemented method of claim 11, wherein the one or more processors are included in a system operated and/or provided by the medical diagnostic provider that completed the medical diagnostic examination for the person.

13. The computer-implemented method of claim 11, wherein the plurality of insurance policy offers includes offers for at least one of a life insurance policy, a long-term care insurance policy, or a disability insurance policy.

14. The computer-implemented method of claim 11, wherein the plurality of insurance policy offers includes different types of insurance policies.

15. The computer-implemented method of claim 11, further comprising:
providing, via the network interface, an indication that the one of the plurality of underwritten binding quotes has been selected to the respective insurance provider computing system.

16. The computer-implemented method of claim 15, further comprising:
receiving an indication that the one of the plurality of underwritten binding quotes has been bound by the respective insurance provider; and
at least one of refunding or crediting to the person a cost of the medical diagnostic examination completed for the person upon receiving the indication that the one of the plurality of underwritten binding quotes has been bound.

17. The computer-implemented method of claim 11, further comprising providing, to the insurance provider computing systems, one or more preferred insurance policy terms in conjunction with the health profile of the person, wherein the insurance provider computing systems generate the plurality of underwritten binding quotes based upon the one or more preferred insurance policy terms.

18. The computer-implemented method of claim 17,
wherein the one or more preferred insurance policy terms include at least one of an amount of a premium payment, a term length, an insurance provider rating, a desired type of insurance, a payout amount, an annuity amount, a settlement option, or another insurance policy term; and
wherein at least one of the one or more preferred insurance policy terms is defined by at least one of the person, an agent of the person, or the insurance provider.

19. The computer-implemented method of claim 11, wherein the medical diagnostic examination performed on the person includes at least one of (i) an invasive procedure, or (ii) is performed as part of an annual physical examination of the person.

20. The computer-implemented method of claim 11, further comprising selecting the plurality of insurance providers based upon the health profile of the person and/or one or more types of insurance.

\* \* \* \* \*